(12) United States Patent
Ragini et al.

(10) Patent No.: US 8,053,090 B2
(45) Date of Patent: *Nov. 8, 2011

(54) PHOSPHORESCENT MULTINUCLEAR COPPER COMPLEX AND ORGANIC ELECTROLUMINESCENT DEVICE USING THE SAME

(75) Inventors: Das Rupasree Ragini, Yongin-si (KR); Hee-Kyung Kim, Yongin-si (KR); Yi-Yeol Lyu, Yongin-si (KR); Young-Hun Byun, Yongin-si (KR); O-Hyun Kwon, Yongin-si (KR); Jhun-Mo Son, Yongin-si (KR); Jung-Bae Song, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 1201 days.

This patent is subject to a terminal disclaimer.

(21) Appl. No.: 11/802,066

(22) Filed: May 18, 2007

(65) Prior Publication Data

US 2007/0270592 A1   Nov. 22, 2007

(30) Foreign Application Priority Data

May 19, 2006 (KR) .......................... 10-2006-0045341
May 10, 2007 (KR) .......................... 10-2007-0045549

(51) Int. Cl.
*H01L 51/54* (2006.01)
*C09K 11/06* (2006.01)

(52) U.S. Cl. . 428/690; 428/917; 313/504; 257/E51.044; 548/101; 546/2; 546/10

(58) Field of Classification Search ........................ None
See application file for complete search history.

(56) References Cited

U.S. PATENT DOCUMENTS

2007/0267959 A1 * 11/2007 Ragini et al. .................. 313/483

FOREIGN PATENT DOCUMENTS

JP  2006-228936 A  *  8/2006

OTHER PUBLICATIONS

Machine translation of JP 2006-228936 (Aug. 2006).*
M. A. Baldo et al., "Highly efficient phosphorescent emission from organic electroluminescent devices", Nature, vol. 395, Sep. 1998, pp. 151-154.
M. A. Baldo et al., "Excitonic singlet-triplet ratio in a semiconducting organic thin film", Physical Review B, vol. 60, No. 20, pp. 14 422-14 428, Nov. 1999.
Mohammad A. Omary et al., "Blue Phosphors of Dinuclear and Mononuclear Copper(I) and Silver(I) Complexes of 3,5-Bis(trifluoromethyl)pyrazolate and the Related Bis(pyrazolyl)borate", Inorganic Chemistry 2003, 42, pp. 8612-8614.

* cited by examiner

*Primary Examiner* — Marie R. Yamnitzky

(57) ABSTRACT

Provided are a high-efficiency phosphorescent multinuclear copper complex and an organic electroluminescent device using the complex. The multinuclear copper complex can be used to form an organic layer of an organic electroluminescent device, and the organic electroluminescent device using the complex can emit light in the yellow to red wavelength region of 560 nm to 630 nm as a high-efficiency photoluminescent material, and provides a high brightness and a low turn-on voltage.

19 Claims, 14 Drawing Sheets

PHOSPHORESCENT MULTINUCLEAR COPPER COMPLEX AND ORGANIC ELECTROLUMINESCENT DEVICE USING THE SAME

CROSS-REFERENCE TO RELATED PATENT APPLICATION AND CLAIM OF PRIORITY

This application claims the benefit of Korean Patent Application Nos. 10-2006-0045341, filed on May 19, 2006 and 10-2007-0045549, filed on May 10, 2007, in the Korean Intellectual Property Office, the disclosure of which is incorporated herein in its entirety by reference.

BACKGROUND OF THE INVENTION

1. Field of the Invention

The present invention relates to a phosphorescent multinuclear copper complex and an organic electroluminescent (EL) device using the same, and more particularly, to a phosphorescent multinuclear copper complex emitting light in the yellow to red wavelength region of 560 nm to 630 nm and an organic electroluminescent device including the multinuclear copper complex as an organic layer forming material.

2. Description of the Related Art

Organic electroluminescent (EL) devices are active display devices using the phenomenon of light generation occurring due to the recombination of electrons and holes in a fluorescent or phosphorescent organic compound thin layer (hereinafter, organic layer) when a current is applied to the organic layer. The organic electroluminescent (EL) devices are lightweight, include simpler and less parts, have a structure that can be manufactured through simple processes, produce high-quality images, and have a wide viewing angle. Organic electroluminescent devices also can produce high-color purity moving pictures, and have low power consumption and a low driving voltage. Therefore, organic electroluminescent devices have electrical characteristics suitable for portable electronic devices.

In general, an organic electroluminescent device has a structure including an anode, a hole transporting layer, an emitting layer, an electron transporting layer, and a cathode, which are sequentially stacked on a substrate. The hole transporting layer, the emitting layer, and the electron transporting layer are organic layers formed of organic compounds. The operating principle of the organic electroluminescent device having such a structure as described above is as follows. When a voltage is applied between the anode and the cathode, holes injected from the anode move to the emitting layer via the hole transporting layer. Electrons are injected from the cathode to the emitting layer via the electron transporting layer. Excitons are generated due to the recombination of carriers in the emitting layer. The excitons undergo radiative decay, emitting light having a wavelength corresponding to the band gap of a material.

Materials for forming the emitting layer of the organic electroluminescent device are classified into fluorescent materials using singlet-state excitons and phosphorescent materials using triplet-state excitons according to the emission mechanism. The emitting layer is formed by doping a fluorescent material or a phosphorescent material directly or doping a fluorescent material or a phosphorescent material on an appropriate host material. As a result of the electron excitation, singlet excitons and triplet excitons are generated in the host. Here, a statistical generation ratio between the singlet excitons and triplet excitons is 1:3 (Baldo, et al., Phys. Rev. B, 1999, 60, 14422).

In an organic electroluminescent device using a fluorescent material as a material for forming the emitting layer, triplet excitons that are generated in the host cannot be used. However, in an organic electroluminescent device using a phosphorescent material as a material for forming the emitting layer, both singlet excitons and triplet excitons can be used, and thus, a 100% internal quantum efficiency can be obtained (Baldo et al., Nature, Vol. 395, 151-154, 1998). Accordingly, the use of a phosphorescent materials leads to a higher light emitting efficiency than when a fluorescent material is used.

When a heavy metal, such as Ir, Pt, Rh, or Pd is included in an organic molecule, spin-orbita coupling occurs due to a heavy atom effect, and thus, singlet excitons and triplet excitons are mixed, thereby enabling the transition and thus effective phosphorescence even at room temperature.

Various materials using a transition metal compound containing a transition metal, such as Iridium (Ir), platinum (Pt), etc. have been reported as high-efficient luminescent materials exhibiting phosphorescence. However, a phosphorescent material emitting light in the yellow to red wavelength region of 560 nm to 630 nm is still required for a high-efficiency, full-color display device.

Pyrazolate ligands are important in the coin metal chemistry. Pyrazolate ligands form a multinuclear complex by coordinating to a metal ion, such as Cu (I), Ag(I), Au(I), etc., in exo-bidentate mode. Coin metal pyrazolates can form a trimer, a tetramer, a hexamer, and up to a polymer according to the reaction condition and the substituent in the pyrazolate moiety. Pyrazolate ligands improve the performance of an organic EL device by functioning as electron transporting moieties assisting the injection of electrons.

Among such coin metal pyrazolates, a multinuclear coin metal having a fluorinated pyrazolate ligand has very interesting light emitting characteristics. Fluorination facilitates thin film formation by assisting volatilization, improves thermal stability and stability of oxidation, and leads to a decrease in emission concentration quenching.

Mohammad (Mohammad A. Omary, Inorg. Chem., 2003, 42, 8612) discloses a metal pyrazolate complex with 2,4,6-cholidine coordinated to copper atoms. This complex emits bright blue light.

In addition, there is a continuous need for the fluorinated metal pyrazolate complex compounds that contain various ligands coordinated to the metal atom in the fluorinated metal pyrazolate complex and that have excellent light emitting characteristics at non-blue wavelength regions.

SUMMARY OF THE INVENTION

The present invention provides a multinuclear copper complex which can efficiently emit light in the yellow to red wavelength region of 560 nm to 630 nm.

The present invention also provides an organic electroluminescent (EL) device using the multinuclear copper complex.

According to an aspect of the present invention, there is provided a multinuclear copper complex represented by Formula 1.

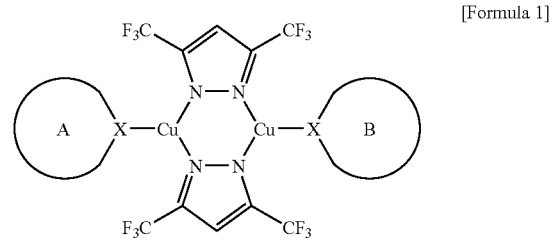

[Formula 1]

where A and B are each independently a $C_2$-$C_6$ heteroaromatic ring containing a hetero atom X and having at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety; and X of A and X of B are independently N, P, S, or O.

The present invention also provides a multinuclear copper complex represented by Formula 2 or Formula 3.

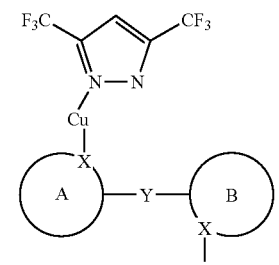

[Formula 2]

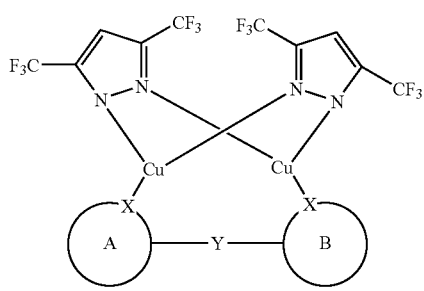

[Formula 3]

where A and B are the same or different and are each a substituted or unsubstituted heteroaromatic ring containing a hetero atom X or a substituted or unsubstituted aliphatic or aromatic group bonded to X, and the substituent of A and B may be at least one of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety;

X of A and X of B are independently N, P, S, or O; and

Y is a bond or a group selected from the group consisting of a substituted or unsubstituted $C_1$-$C_{20}$ alkylene group, a substituted or unsubstituted $C_6$-$C_{20}$ arylene group, a substituted or unsubstituted $C_5$-$C_{20}$ cycloalkylene group, a substituted or unsubstituted $C_1$-$C_{20}$ heteroarylene group, a silyl group, and a boryl group.

Each of A (i.e.

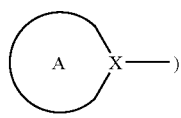

and B (i.e.,

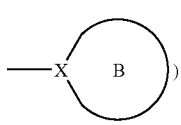

in Formula 1 may be independently represented by one of the following formulae below.

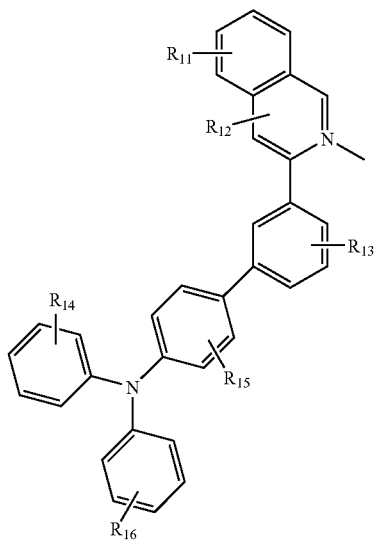

[Formula 4]

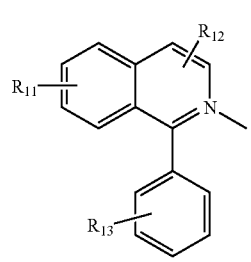

[Formula 5]

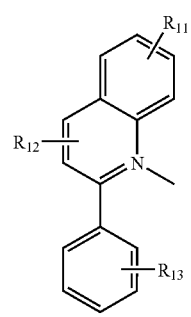

[Formula 6]

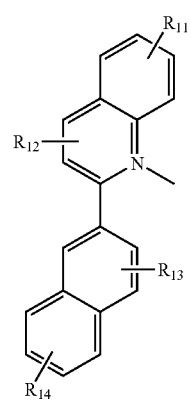

[Formula 7]

[Formula 8]

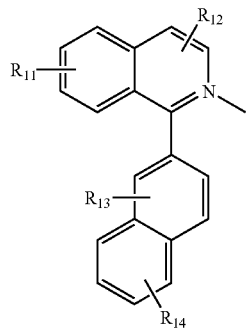

[Formula 9]

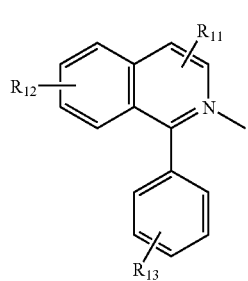

[Formula 10]

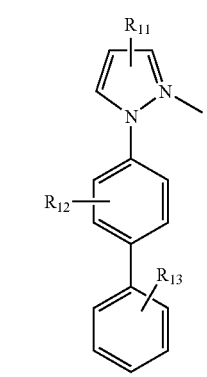

[Formula 11]

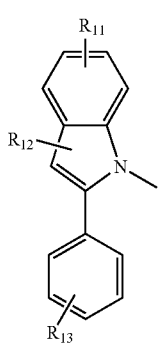

[Formula 12]

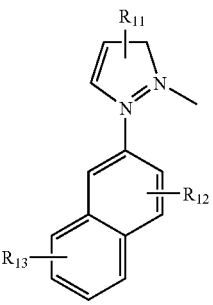

[Formula 13]

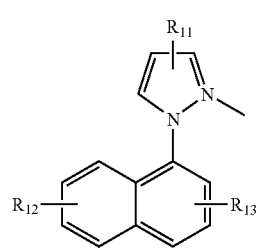

[Formula 14]

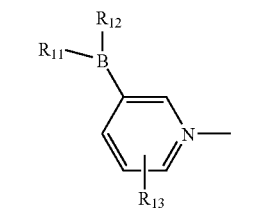

In Formula 4 through 14 above, $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The multinuclear copper complex represented by Formula 1 may be one of compounds represented by Formula 15 and 16.

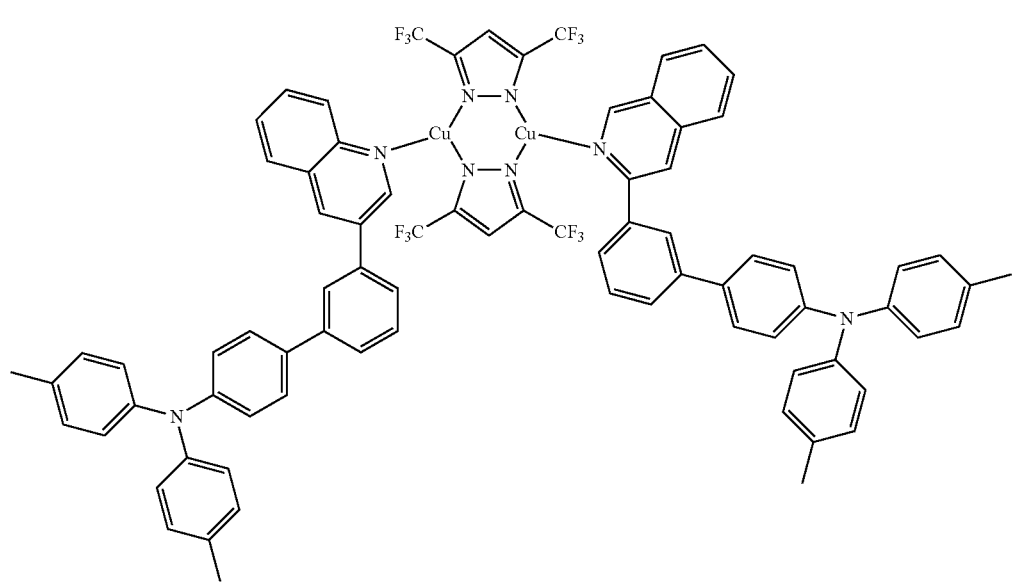
[Formula 15]
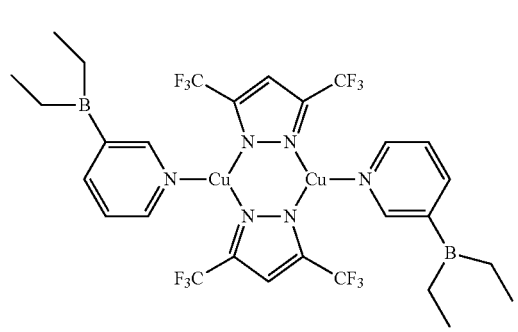
[Formula 16]
In Formula 2 or Formula 3 above,
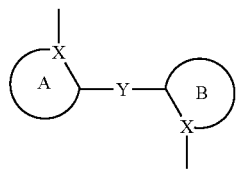
may be one of the groups represented by Formula 17 through 19 below.
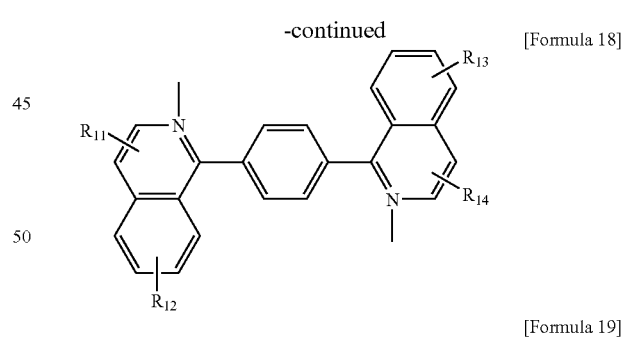
[Formula 18]
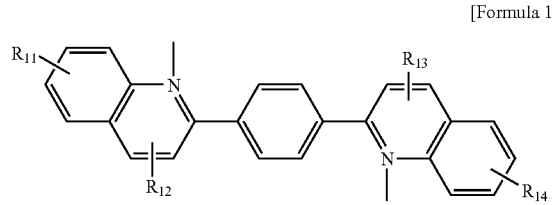
[Formula 17]
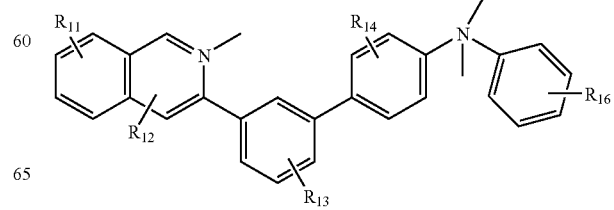
[Formula 19]

In Formula 17 through 19 above, $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The multinuclear copper complex represented by Formula 2 may be one of compounds represented by Formula 20 through 22.

[Formula 20]

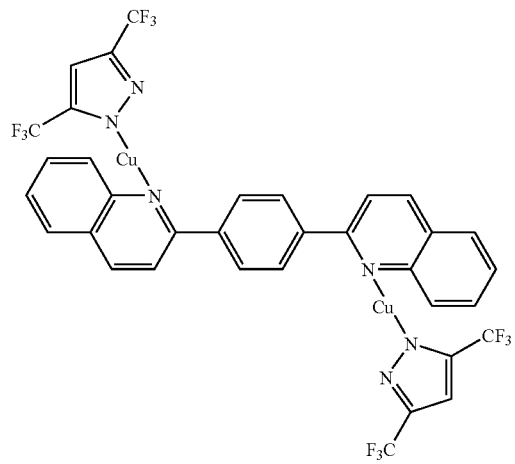

[Formula 21]

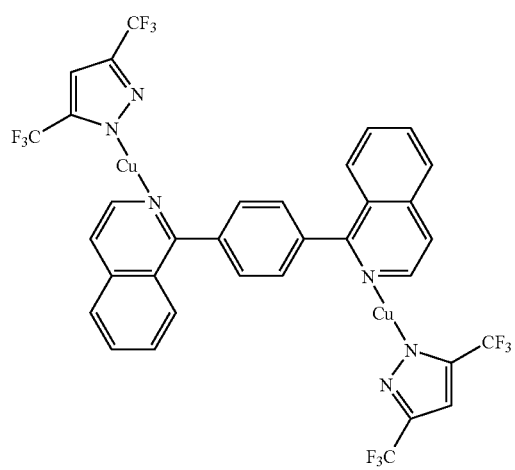

[Formula 22]

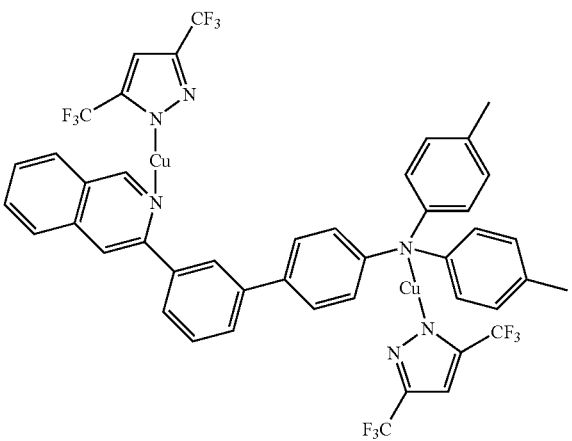

The multinuclear copper complex represented by Formula 3 may be one of compounds represented by Formula 23 to 25.

[Formula 23]

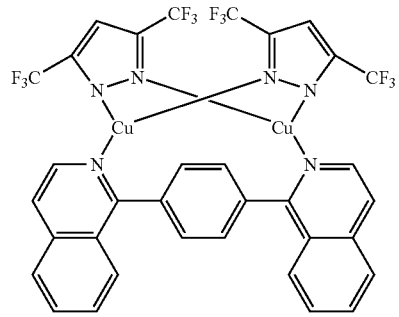

[Formula 24]

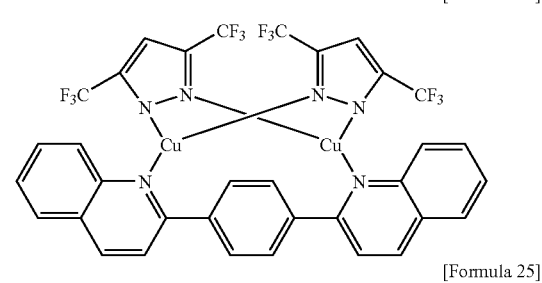

[Formula 25]

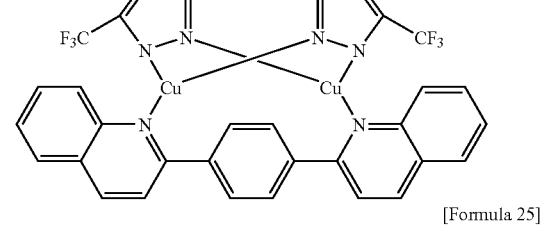

According to another aspect of the present invention, there is provided an organic EL device comprising an organic layer between a pair of electrodes, the organic layer containing one of the multinuclear copper complexes described above.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
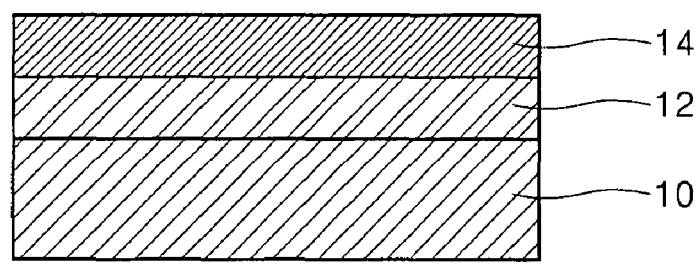
FIGS. 1A through 1F are diagrams schematically illustrating laminated structures of organic electroluminescent (EL) devices according to embodiments of the present invention.

Hereinafter, embodiments of the present invention will be described in detail.

The present invention provides multinuclear copper complexes represented by Formula 1 thorugh 3. The performance of the devices utilizing the copper complexes including a metal pyrazolate ligand is improved, due to the excellent electron transport ability of pyrazole. In addition, due to a heteroaromatic ring coordinated to a copper atom, the charge transport ability is excellent.

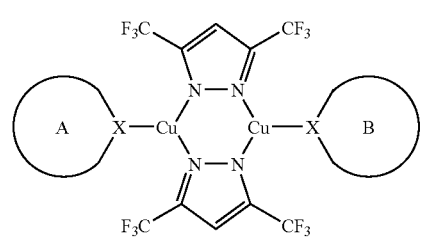
[Formula 1]

In Formula 1, A and B are each independently a $C_2$-$C_6$ heteroaromatic ring containing a hetero atom X and having at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety; and X of A and X of B are independently N, P, S, or O.

The term "C2-C6 heteroaromatic ring" includes a C2-C6 heteroaromatic ring with a fused ring as well as a single aromatic ring. For example, the C2-C6 heteroaromatic ring may include quinoline (i.e., an analog of pyridine with a fused benzene ring) or indole (i.e., an analog of pyrrole with a fused benzene ring) as well as pyridine or pyrrole.

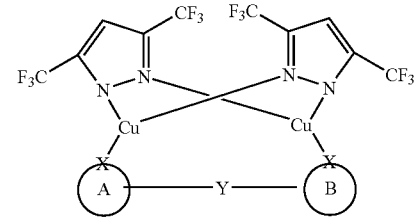
[Formula 2]

[Formula 3]

In Formula 2 or 3, A and B are the same or different and are each a substituted or unsubstituted heteroaromatic ring containing a hetero atom X or a substituted or unsubstituted aliphatic or aromatic group bonded to X, and the substituent of A and B may be at least one of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety;

X of A and X of B are independently N, P, S, or O; and

Y is a bond or a group selected from the group consisting of a substituted or unsubstituted $C_1$-$C_{20}$ alkylene group, a substituted or unsubstituted $C_6$-$C_{20}$ arylene group, a substituted or unsubstituted $C_5$-$C_{20}$ cycloalkylene group, a substituted or unsubstituted $C_1$-$C_{20}$ heteroarylene group, a silyl group, and a boryl group.

In Formula 3, a copper atom is in +1 oxydation state having coordination number 3 with a distorted trigonal planar structure. Each Cu(I) is coordinated to the negatively charged N of one imidazole, neutral nitrogen of the second imidazole and X. Each of A (i.e.,

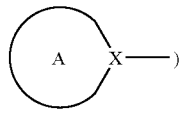

and B (i.e.,

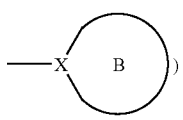

in Formula 1 may be independently one of the following formulae below.

[Formula 4]

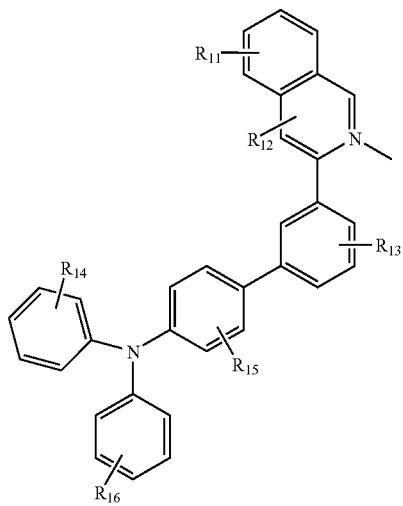

[Formula 5]

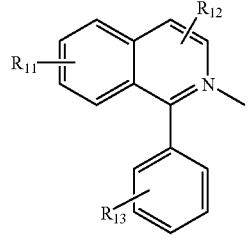

[Formula 6]

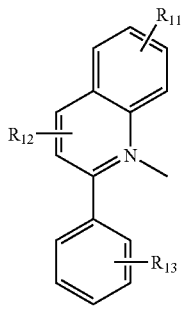

[Formula 7]

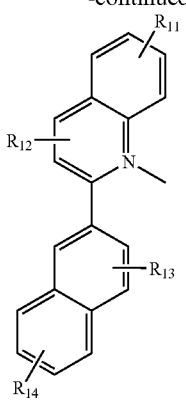

[Formula 8]

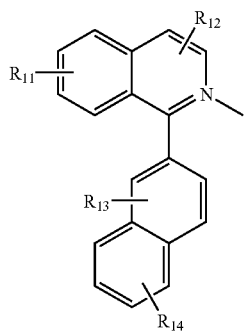

[Formula 9]

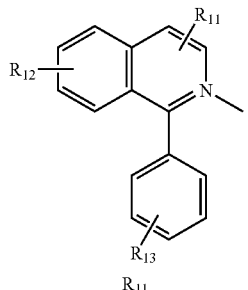

[Formula 10]

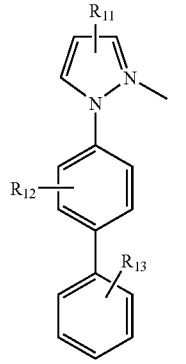

[Formula 11]

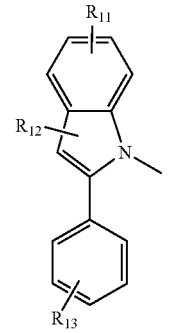

[Formula 12]

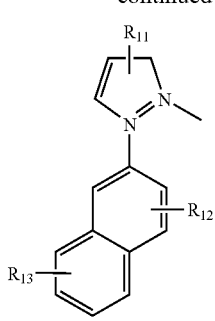

[Formula 13]

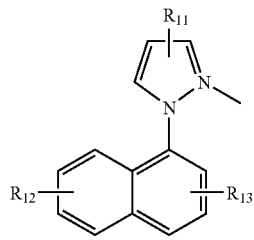

[Formula 14]

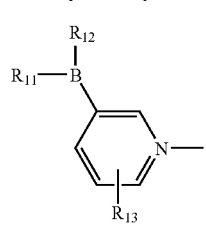

In Formula 4 through 14 above, $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The multinuclear copper complex represented by Formula 1 may be one of compounds represented by Formula 15 and 16.

[Formula 15]

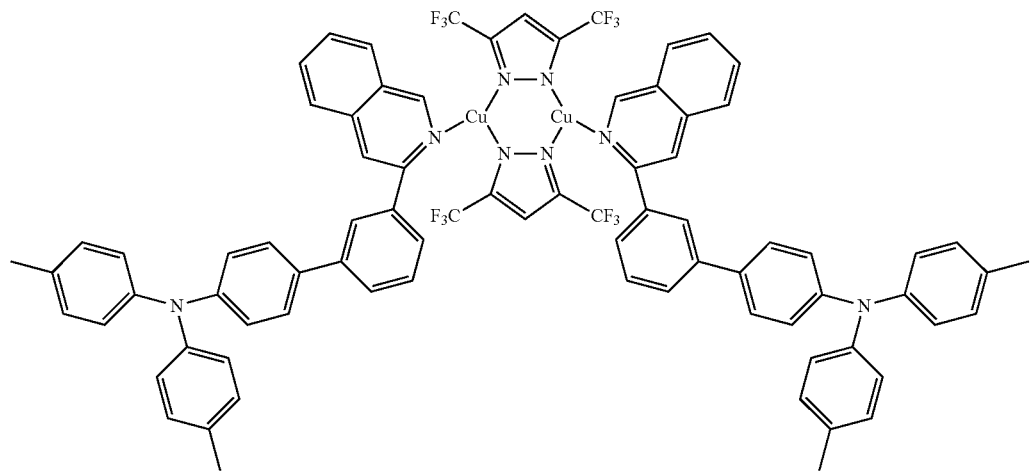

[Formula 16]

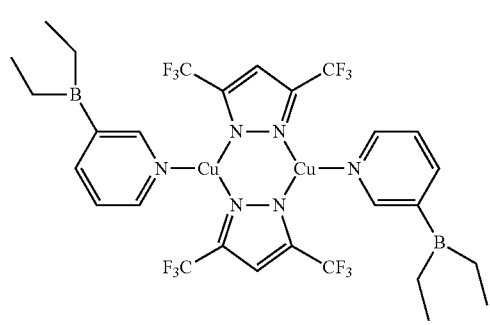

In Formula 2 above,

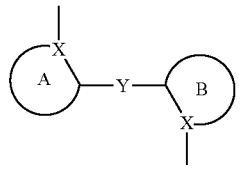

may be one of the groups represented by Formula 17 through 19 below.

[Formula 17]

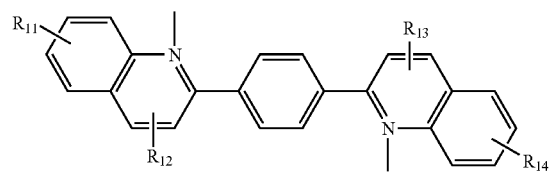

[Formula 18]

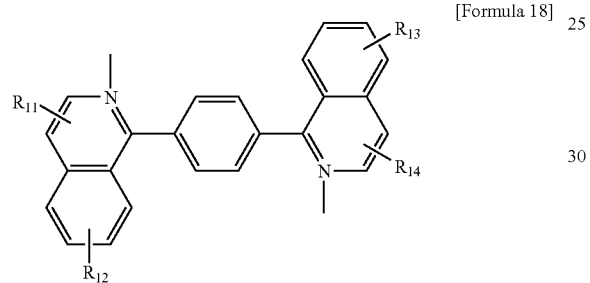

[Formula 19]

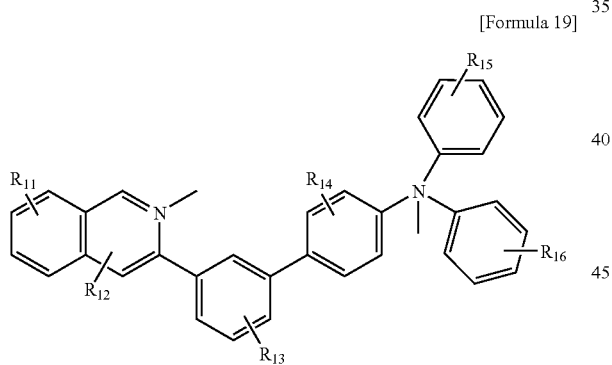

In Formula 17 through 19 above, $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The multinuclear copper complex represented by Formula 2 may be one of compounds represented by Formula 20 through 22.

[Formula 20]

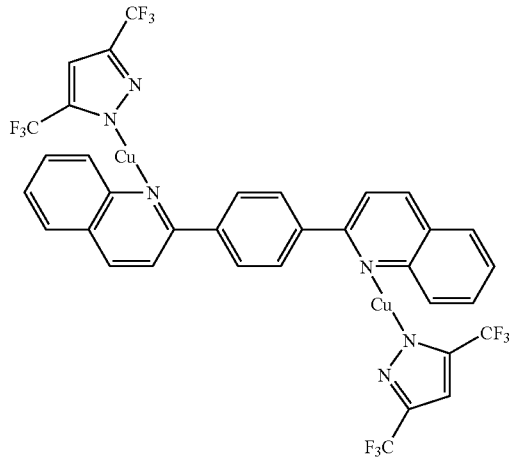

[Formula 21]

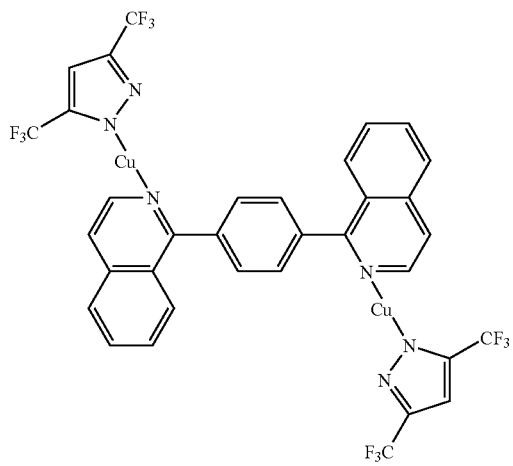

[Formula 22]

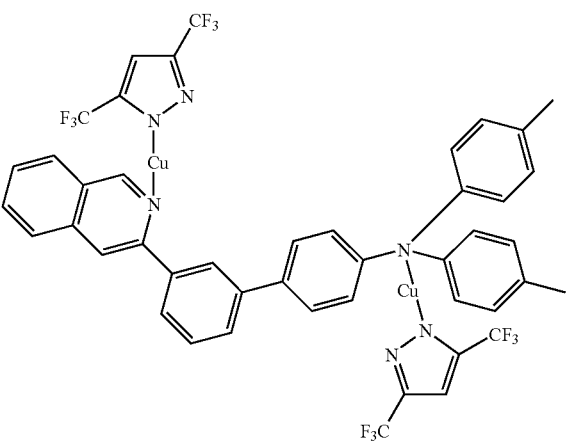

The multinuclear copper complex represented by Formula 3 may be one of compounds represented by Formula 23 to 25.

[Formula 23]

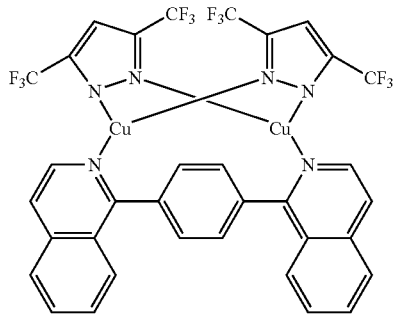

[Formula 24]

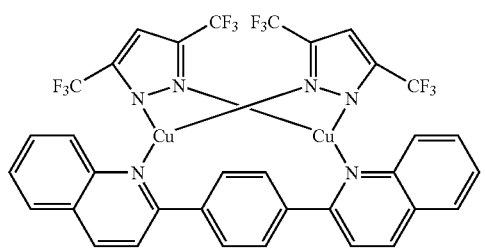

[Formula 25]

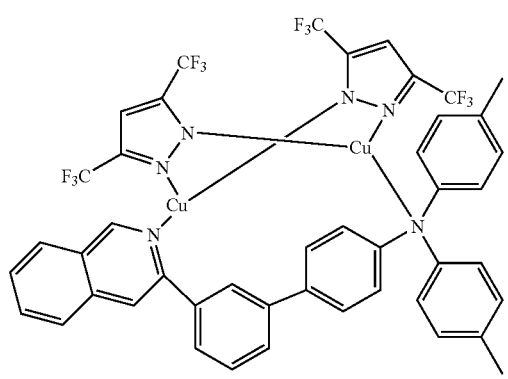

In Formula 1, examples of substituents of A and B include: a $C_5$-$C_{20}$ cycloalkyl group, such as cyclohexyl, cyclopentyl, cyclooctyl, etc.; a $C_6$-$C_{20}$ aryl group, such as phenyl, 1,3-benzodioxole, biphenyl, naphthalene, anthracene, azulene, etc.; a $C_1$-$C_{20}$ heteroaryl group, such as thiophene, furan2 (5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl)pyrazole, 2,5-bisphenyl-1,3,4-oxadiazole, 2,3-benzofurane2-(4-biphenyl)-6-phenyl benzooxazole, etc.

Examples of a silyl group include triarylsilyl, trialkylsilyl, etc. Examples of a boryl group include dialkylboryl, diarylboryl, difluoroboryl, difluoroheteroarylboryl, etc.

Examples of the hole transporting moiety include quinolyl, substituted quinolyl, imidazolyl, substituted imidazolyl, benzimidazolyl, triazolyl, substituted triazolyl, oxazolyl, substituted oxazolyl, 1,10-phenantrolyl, substituted 1,10-phenantrolyl, quinoxalinyl, substituted quinoxalinyl, etc.

Examples of the aliphatic or aromatic compound bonded to X for A and B in Formula 2 or 3 above include a $C_5$-$C_{20}$ alkyl group, a $C_6$-$C_{20}$ aryl group, a $C_1$-$C_{20}$ heteroaryl group, a $C_3$-$C_{20}$ cycloalkyl group, etc.

The multinuclear copper complex represented by Formula 1 according to an embodiment of the present invention can be synthesized by reacting a compound $\{[3,5-(CF_3)_2Pz]Cu\}_3$ (where Pz is pyrazole) of Formula 26 below with heteroaromatic ring compounds represented by Formula 27 and 28.

[Formula 26]

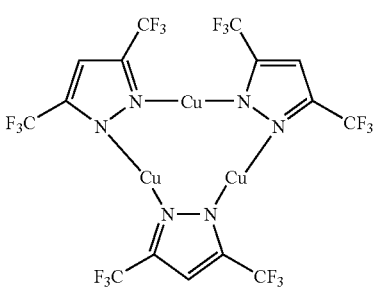

[Formula 27]

A — X

[Formula 28]

X — B

In Formula 27 and 28, A, B, and X are the same as defined in connection with Formula 1 above.

A method of preparing a exemplary compound of Formula 1 is illustrated in Reaction Scheme 1 below.

<Reaction Scheme 1>
Synthesis of $\{[3,5-(CF_3)_2 Pz]Cu[diethylpyridyl\ borane]\}_2$

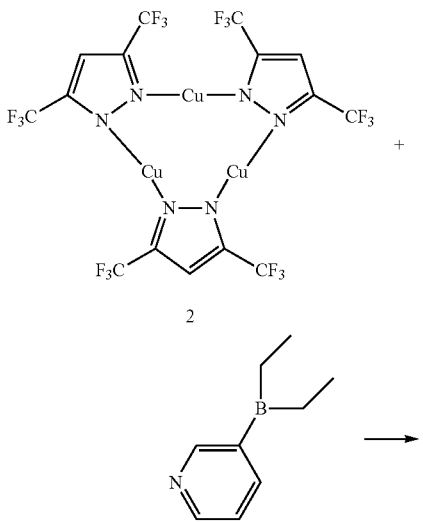

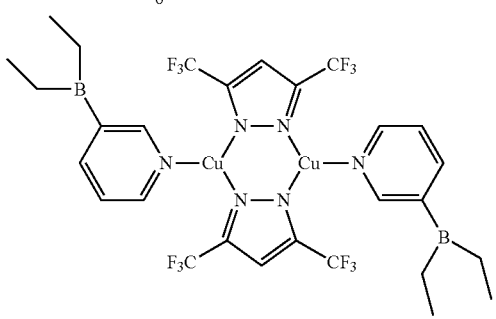

The reaction in Reaction Scheme 1 may be performed in a solvent, such as benzene, in a mole ratio of 1:3 between the compound of Formula 26 and diethylpyridyl borane at 25 to 40° C. for 24 to 48 hours.

The multinuclear copper complex represented by Formula 2 or 3 according to an embodiment of the present invention can be synthesized by reacting the compound {[3,5-(CF$_3$)$_2$Pz]Cu}$_3$ of Formula 26 with a compound of Formula 29:

[Formula 29]

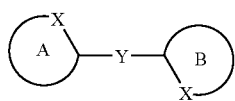

In Formula 29 above, A, B, X, and Y are the same as defined in connection with Formula 2 or 3 above.

The compounds of Formula 2 and 3, which are valence isomers, are obtained together through the above reaction. It may be possible that both the structures exist in solution as the solvents help in the crossover of the secondary valency 2 of Cu(I) in Formula 2 to the secondary valency 3 of Cu(I) in Formula 3.

A method of preparing a representative compound of Formula 2 or 3 is illustrated in Reaction Scheme 2 below.

<Reaction Scheme 2>
Synthesis of
{[3, 5-(CF$_3$)$_2$Pz]Cu[4-(2-isoquinolyl)biphenylditoluyl amine]}$_2$

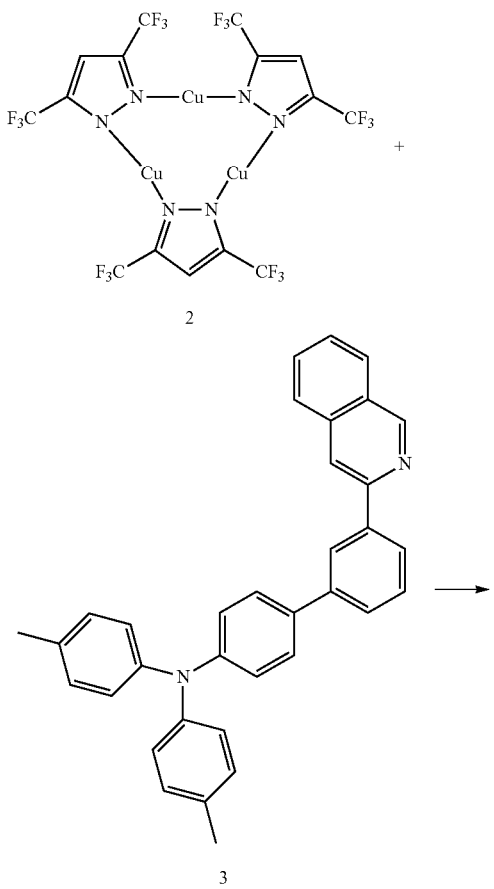

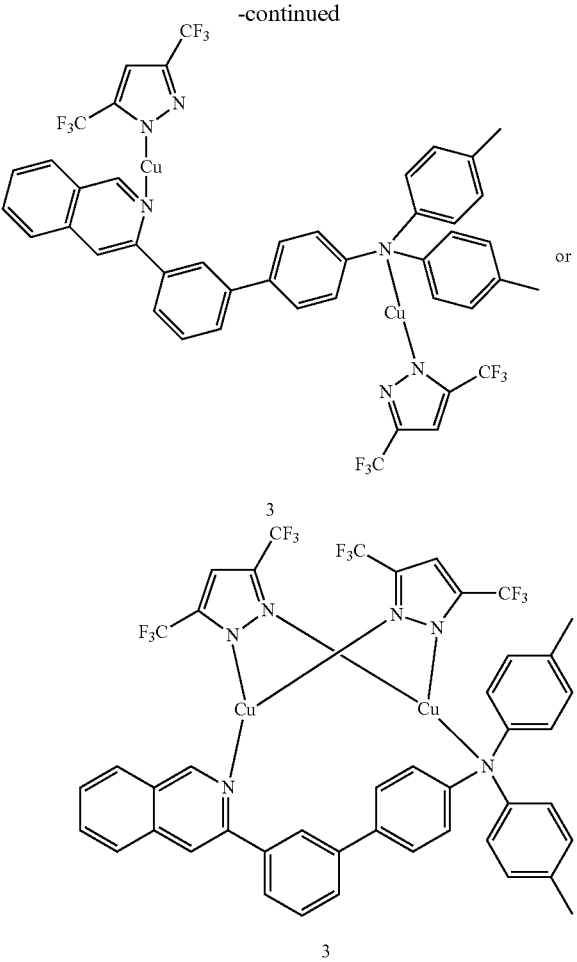

The reaction in Reaction Scheme 2 may be performed in a solvent, such as benzene, in a mole ratio of 2:3 between the compound of Formula 26 and the compound of Formula 29 at 25-40° C. for 24-48 hours.

An organic EL device according to an embodiment of the present invention includes an organic layer, and in particular, an emitting layer, formed of one of the copper complexes of Formula 1 thorugh 3. Here, the copper complexes of Formula 1 thorugh 3 are very useful phosphorescent dopants used to form the emitting layer and exhibit excellent light emitting characteristics in the yellow to red wavelength region of 560 nm to 630 nm.

When the copper complexes represented by Formula 1 thorugh 3 are used as phosphorescent dopants, the organic layer may further include at least one host selected from the group consisting of a polymer host, a mixed host of a polymer and a low-molecular weight material, a low-molecular weight host, and a non-emitting polymer matrix. Here, any polymer host, low-molecular weight host, and non-emitting polymer matrix which are commonly used to form the emitting layer of an organic EL device can be used. Examples of the polymer host include poly(vinylcarbazole) (PVK), polyfluorene, etc., but are not limited thereto. Examples of the low-molecular weight host include CBP(4,4'-N,N'-dicarbazole-biphenyl), 4,4'-bis[9-(3,6-biphenylcarbazolyl)]-1-1,1'-biphenyl, 9,10-bis[(2',7'-t-butyl)-9',9"-spirobifluorenyl anthracene, terafluorene, etc. but are not limited thereto. Examples of the non-emitting polymer matrix include polymethylmethacrylate, polystyrene, etc., but are not limited thereto.

The amount of the copper complex represented by one of Formula 1 thorugh 3 may be, for example, in a range of 1 to 30 parts by weight based on 100 parts by weight of the emitting layer forming material. When the amount of the copper complex is less than 1 part by weight, the amount of the luminescent material is insufficient, and thus, the efficiency and lifetime decrease. When the amount of the copper complex is above 30 parts by weight, triplet excitons quench, and thus, the efficiency decreases. In addition, when incorporating the copper complex into the emitting layer, various methods, such as vacuum deposition, sputtering, printing, coating, ink-jetting, etc. can be used.

Moreover, when the multinuclear copper complexes represented by Formula 1 thorugh 3 can emit white light when used together with a green luminescent material or a blue luminescent material.

FIGS. 1A through 1F are diagrams schematically illustrating laminated structures of organic EL devices according to embodiments of the present invention.

Referring to FIG. 1A, an emitting layer 12 containing the copper complex of one of Formula 1 thorugh 3 is formed on a first electrode 10, and a second electrode 14 is formed on the emitting layer 12.

Figure 1B:
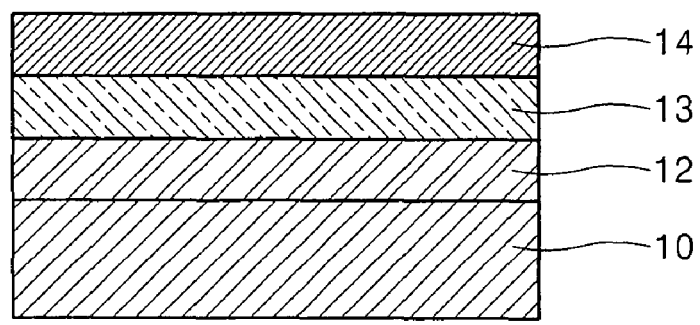

Referring to FIG. 1B, the emitting layer 12 containing the copper complex of one of Formula 1 thorugh 3 is formed on the first electrode 10, a hole blocking layer (HBL) 13 is formed on the emitting layer 12, and the second electrode 14 is formed on the HBL 13.

Figure 1C:
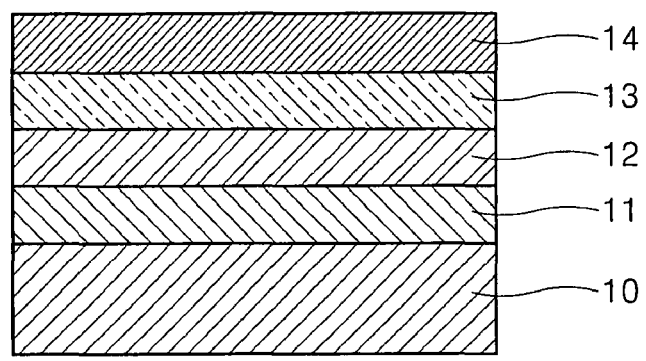

An organic EL device in FIG. 1C further includes a hole injecting layer (HIL) 11 formed between the first electrode 10 and the emitting layer 12.

Figure 1D:
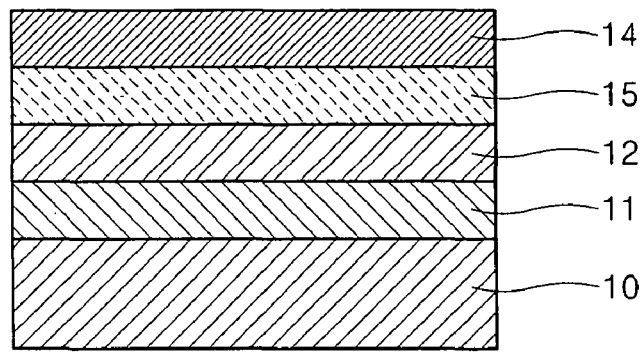

An organic EL device in FIG. 1D has the same laminated structure as the organic EL device in FIG. 1C, except that an electron transporting layer (ETL) 15 instead of the HBL 13 is formed on the emitting layer 12.

Figure 1E:
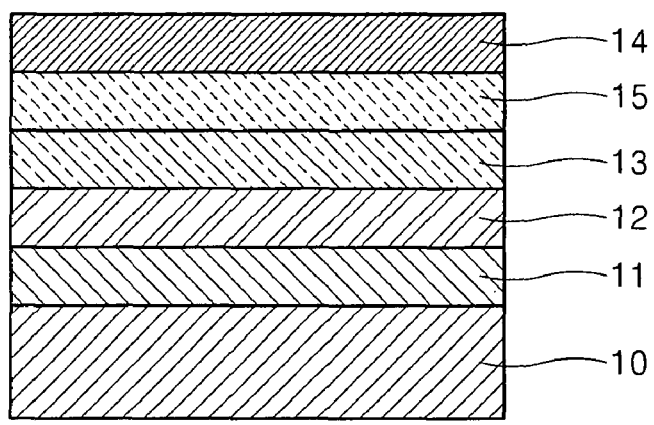

An organic EL device in FIG. 1E has the same laminated structure as the organic EL device in FIG. 1C, except that two layers, i.e., the HBL 13 and the ETL 15, instead of the single HBL 13, are sequentially formed on the emitting layer 12 containing the copper complex of one of Formula 1 thorugh 3. The organic EL device of FIG. 1E may further include an electron injecting layer between the ETL 15 and the second electrode 14 if required.

Figure 1F:
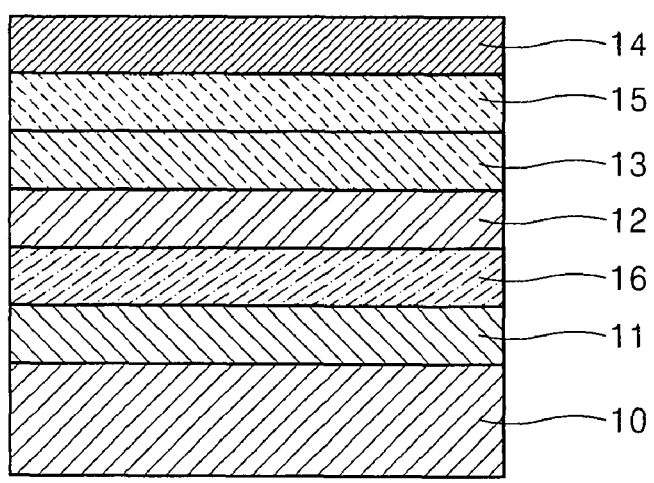

An organic EL device of FIG. 1F has the same structure as the organic EL device of FIG. 1E, except that a hole transporting layer (HTL) 16 is further formed between the HIL 11 and the emitting layer 12. The HTL 16 prevents entering of impurities from the HIL 11 into the emitting layer 12.

An organic EL device having such a laminated structure as described above may be manufactured using a general method without limitations.

The organic layer may have a thickness of organic layer 30-100 nm. When the thickness of the organic layer is smaller than 30 nm, the efficiency and lifetime thereof decrease. When the thickness of the organic layer is greater than 100 nm, the operating voltage increases.

Here, the organic layer means a layer formed of an organic compound between a pair of electrodes in an organic EL device. For example, the organic layer may be the emitting layer, the electron transporting layer, the hole transporting layer, etc.

In the organic EL device, a buffer layer may be each interposed between the layers. A material for the buffer layer can be any material commonly used in the field. Examples of a material for the buffer layer common include copper phthalocyanine, polythiophene, polyaniline, polyacetylene, polypyrrole, polyphenylene vinylene, and a derivative thereof, but are not limited thereto.

A material for the hole transporting layer (HTL) can be any material commonly used in the field, for example, polytriphenylamine, but is not limited thereto.

A material for the electron transporting layer (ETL) can be any material commonly used in the field, for example, polyoxadiazole, but is not limited thereto.

A material for the hole blocking layer (HBL) can be any material commonly used in the field, for example, LiF, $BaF_2$, or $MgF_2$, but is not limited thereto.

An organic EL device according to an embodiment of the present invention can be manufactured without using a special equipment and method. For example, an organic EL device according to an embodiment of the present invention can be manufactured according to a method of manufacturing an organic EL device using a common luminescent material.

The copper complexes of Formula 1 thorugh 3 according to an embodiment of the present invention can emit light having a wavelength of about 560 nm to 630 nm. A light emitting diode using the copper complex can be used in a light source for full-color display, a backlight, an outdoor board, optical communication, interior decoration, etc.

Hereinafter, the present invention will be described in greater detail with reference to the following examples. The following examples are for illustrative purposes only and are not intended to limit the scope of the invention.

Reference Example 1

Synthesis of $\{3,5\text{-}(CF_3)_2Pz\}\}Cu_3\}$

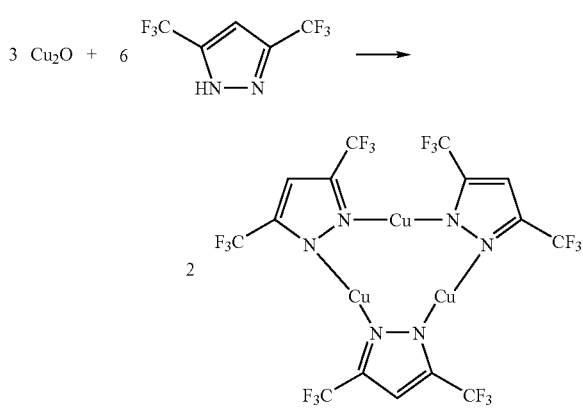

0.40 g (1.90 mmole) of $Cu_2O$ and 1 g (4.9 mmole) of 3,5-trifluoromethyl pyrazole were added to 20-30 mL of benzene and reacted at 60° C. for 48 to 72 hours. The reaction product was cooled and filtered at a reduced pressure, and the solvent was evaporated from the reaction mixture. Resulting white powder was recrystallized using a mixture of benzene and hexane.

$^1$H NMR $CDCl_3$: ppm 6.97 (s, 1H, CH), 13.07-11.23 (broad, NH)

Example 1

Synthesis of Compound ({[3,5-(CF$_3$)$_2$Pz]Cu[4-(2-isoquinolyl)biphenyl ditoluyl amine]}$_2$) of Formula 22 and 25

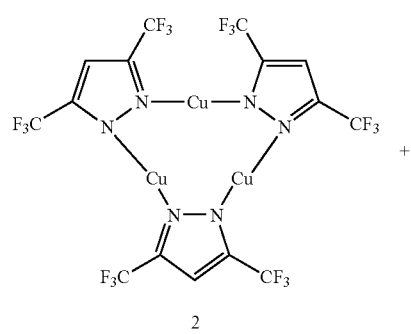

2

+

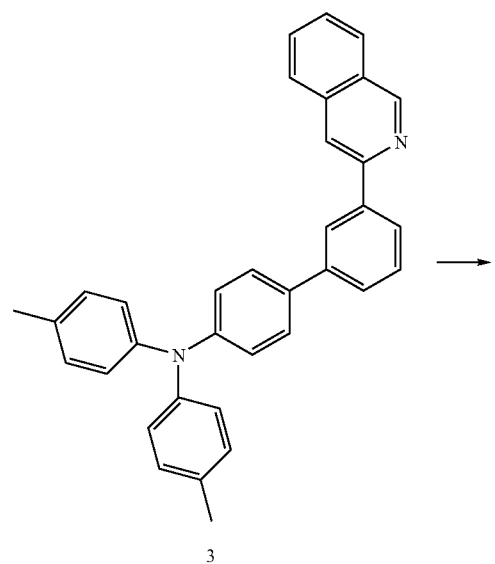

3

→

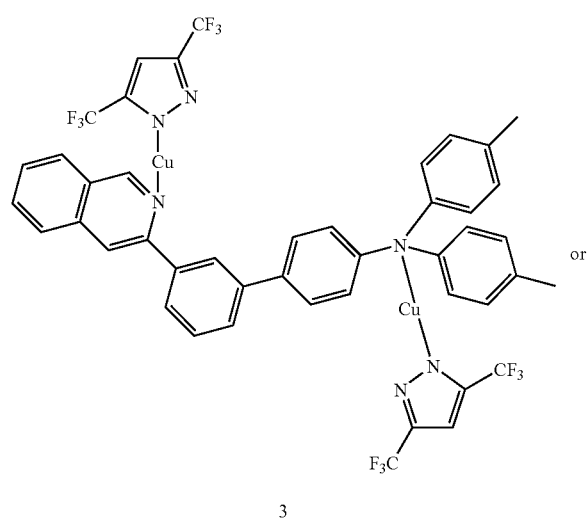

3 or

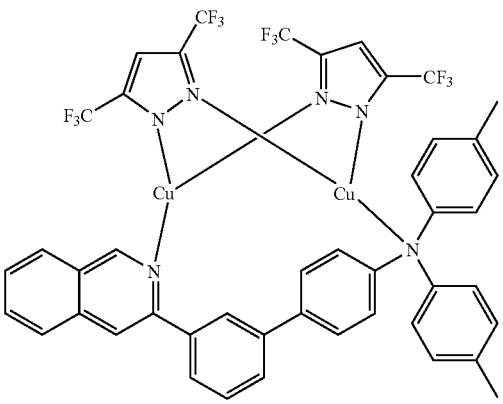

3

Figure 3:
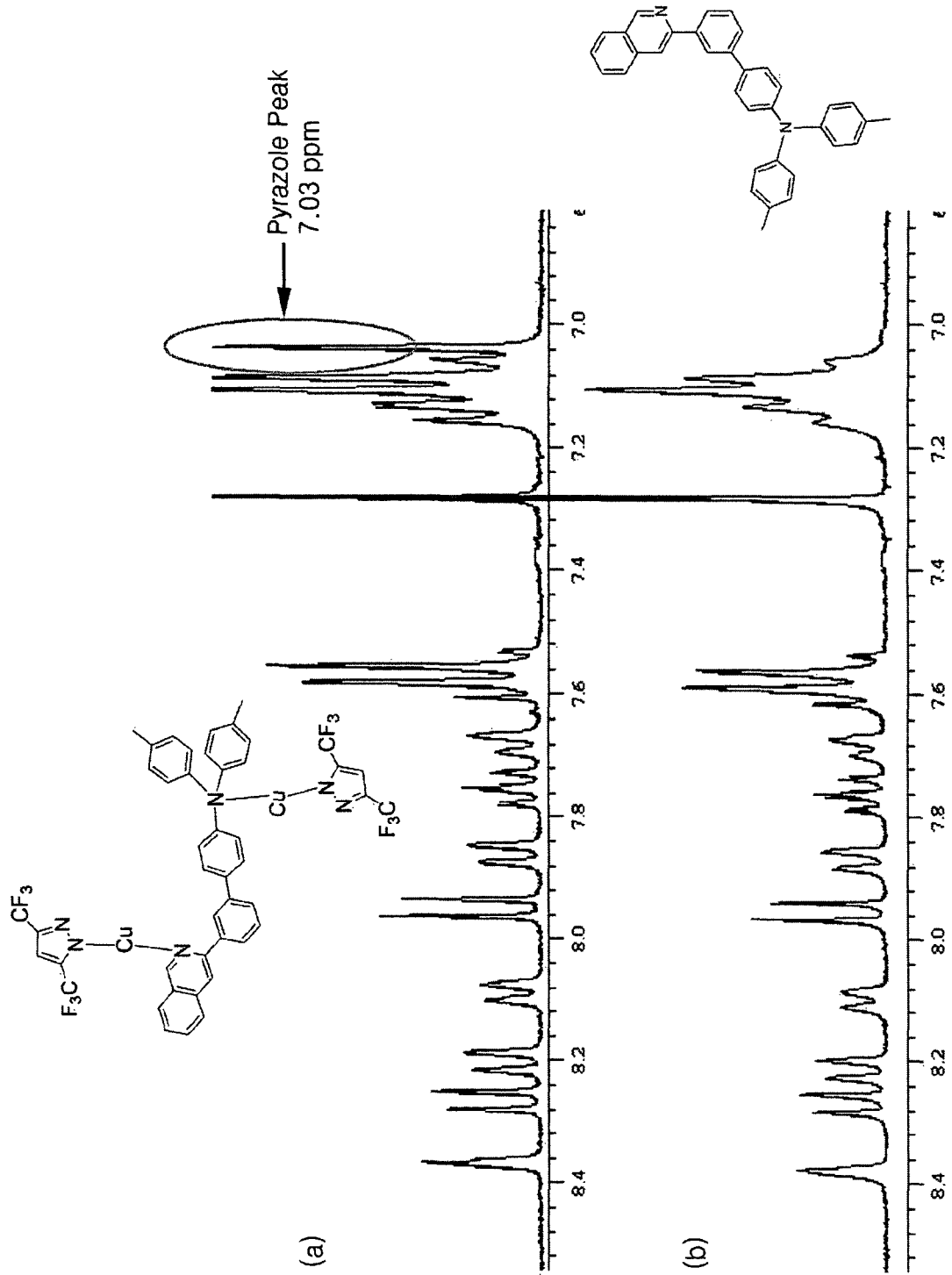
FIG. 3 is NMR spectra of a phosphorescent multinuclear copper complex (a) synthesized in Example 1 and isoquinoline phenyltriphenyl amine (b)

0.160 g (0.2 mmol) of {3,5-(CF$_3$)$_2$Pz}-Cu$_3$} synthesized in Reference Example 1 was reacted with 0.111 g (0.3 mmol) of isoquinolylbipheylditoluylamine in 30 mL of benzene for 48 hours. After the reaction terminated, the reaction solution was filtered using Celite and precipitated in hexane to obtain a greenish yellow solid compound of Formula 22 and 25. The greenish yellow solid powder was washed with hexane several times and reprecipitated using a solution of benzene and hexane. The structure of the final product was analyzed and identified through $^1$H NMR spectroscopy. The results are shown in FIG. 3. In FIG. 3, (a) is an NMR spectrum of the multinuclear copper complex of Formula 22 and 25, and (b) is an NMR spectrum of isoquinolylbiphenylditoluylamine. Comparing the two NMR spectra, a pyrazole peak appeared in (a), indicating that the compounds of Formula 22 and 25 were synthesized.

$^1$H NMR CDCl$_3$: ppm 8.37 (s, 1H), 8.26 (d, 1H), 8.18 (d, 1H), 8.08 (d, 1H), 7.94 (d, 1H), 7.85 (d, 1H), 7.75 (t, 1H), 7.68 (d, 1H), 7.57 (dd, 4H), 7.2-7.04 (m, 10H), 7.03 (s, 2H)

$^{19}$F NMR CDCl$_3$: ppm 61.23

The NMR data shows the possibility of the formation of the above two structures. The above two structures are the valence isomers. It may be possible that both the structures exist in solution as the solvents help in the crossover of the secondary valency 2 of Cu(I) in the first structure to the secondary valency 3 of Cu(I) in the second structure.

Example 2

Synthesis of Compound ({[3,5-(CF$_3$)$_2$ Pz]Cu[diethyl pyridyl borane]}$_2$ of Formula 16

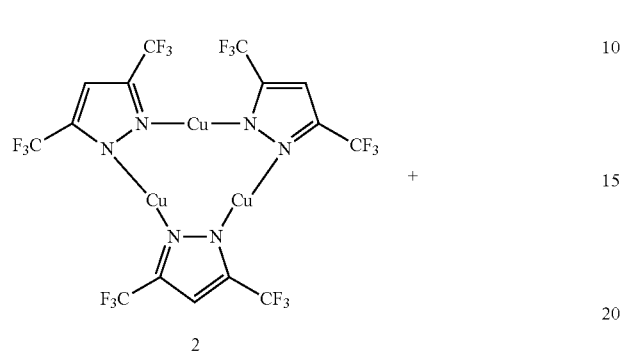

2

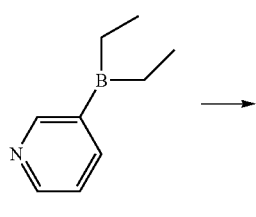

6

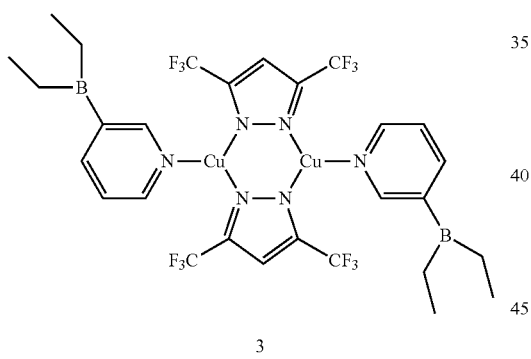

3

0.160 g (0.2 mmol) of {3,5-(CF$_3$)$_2$Pz}-Cu$_3$} synthesized in Reference Example 1 was reacted with 0.177 g (1.2 mmol) of diethylborylpyridine in 30 mL of benzene for 48 hours. After the reaction terminated, the reaction solution was filtered using Celite and precipitated in hexane to obtain a colorless solid compound of Formula 16. The colorless solid powder was washed with hexane several times and reprecipitated using a solution of benzene and hexane. The structure of the final product was analyzed and identified through $^1$H NMR spectroscopy.

$^1$H NMR CDCl$_3$: ppm 8.66 (s, 1H), 8.50 (d, 1H), 7.7(d, 1H), 7.2 (t, 1H), 1.2 (m, 4H), 0.30 (m, 6H)

$^{19}$F NMR CDCl$_3$: ppm −61.30

Example 3

Synthesis of Compound {[3,5-(CF$_3$)$_2$Pz]Cu}$_2$[1,4-bis(2-isoquinolyl)benzene] of Formula 21 and Formula 23

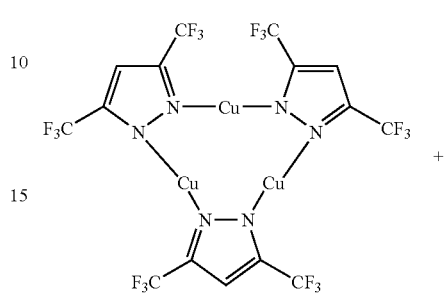

2

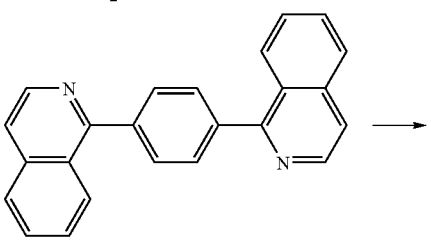

3

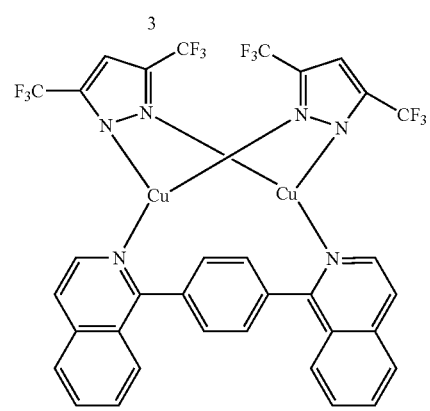

3

Figure 9:
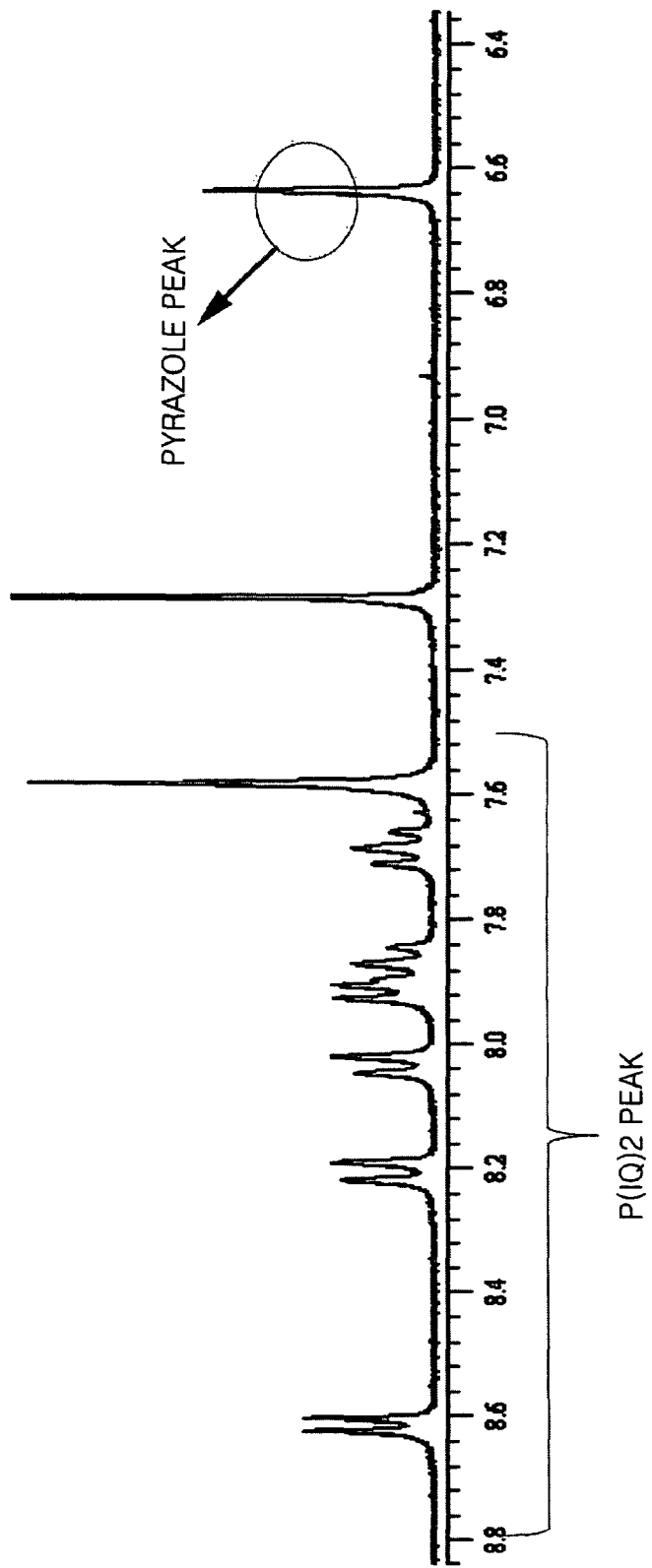
FIG. 9 is an NMR spectrum of the phosphorescent multinuclear copper complex obtained in Example 3.
Figure 10:
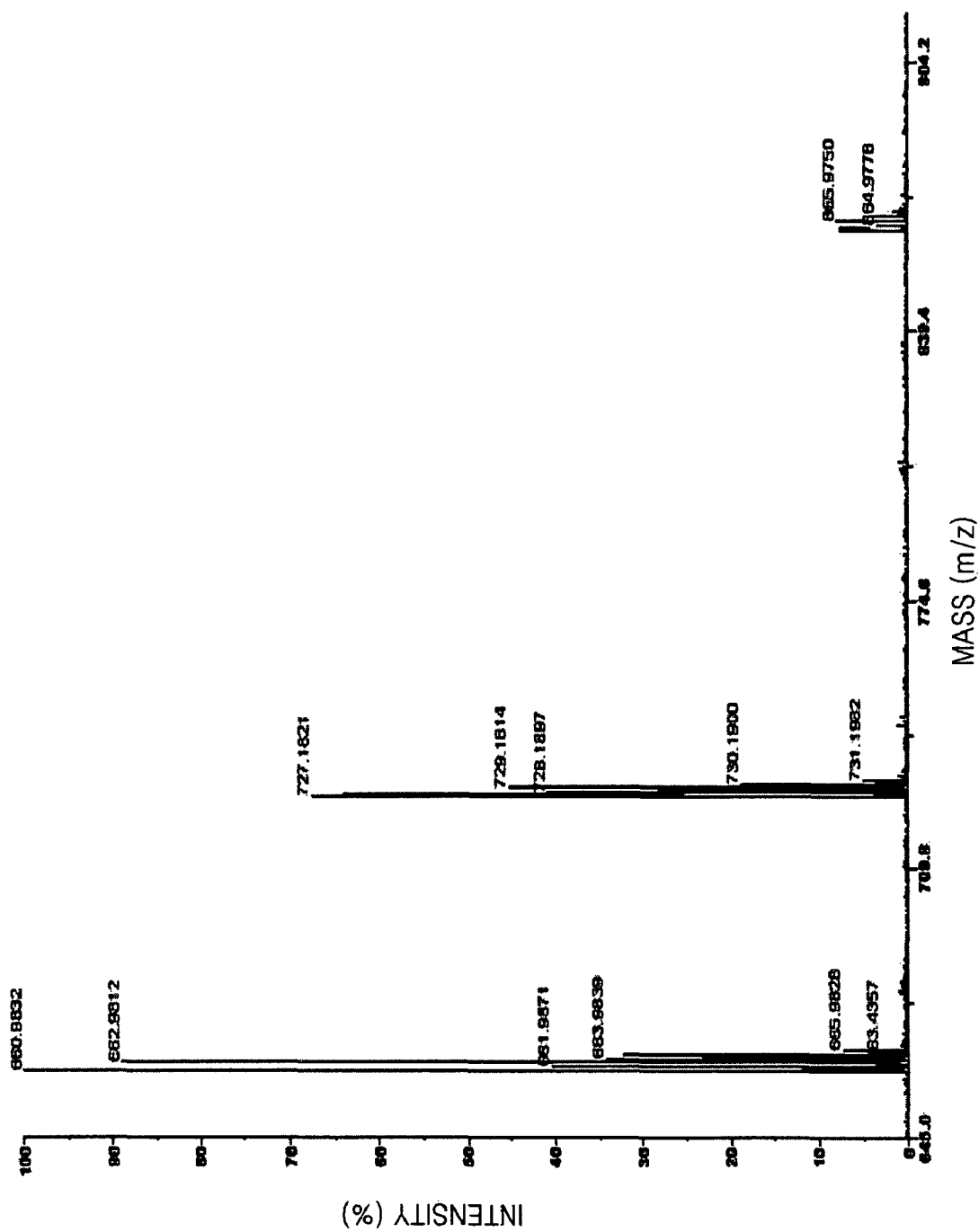
FIG. 10 is an mass spectrum of the phosphorescent multinuclear copper complex obtained in Example 3.

0.160 g (0.2 mmol) of {3,5-(CF$_3$)$_2$Pz}-Cu$_3$} synthesized in Reference Example 1 was reacted with 0.1 g (0.3 mmol) of phenyldiisoquinoline in 30 mL of benzene for 48 hours. After the reaction terminated, the reaction solution was filtered using Celite and precipitated in hexane to obtain a yellow solid compound of Formula 21 and 23. The yellow solid powder was washed with hexane several times and reprecipitated using a solution of benzene and hexane. The structure of the final product was analyzed and identified through $^1$H NMR spectroscopy. The results are shown in FIGS. 9 and 10. In FIG. 9, a pyrazole peak, in addition to a phenyldiisoquinoline peak, appeared, indicating the compounds of Formula 21 and 23 were synthesized.

$^1$H NMR CDCl$_3$: ppm 8.61 (d, 1H), 8.20 (d, 1H), 8.03 (d, 1H), 7.94-7.83 (m, 2H), 7.68 (t, 1H), 7.58 (s, 2H), 6.6 (s, 1H)

$^{19}$F NMR CDCl$_3$: ppm −61.00

Figure 12:
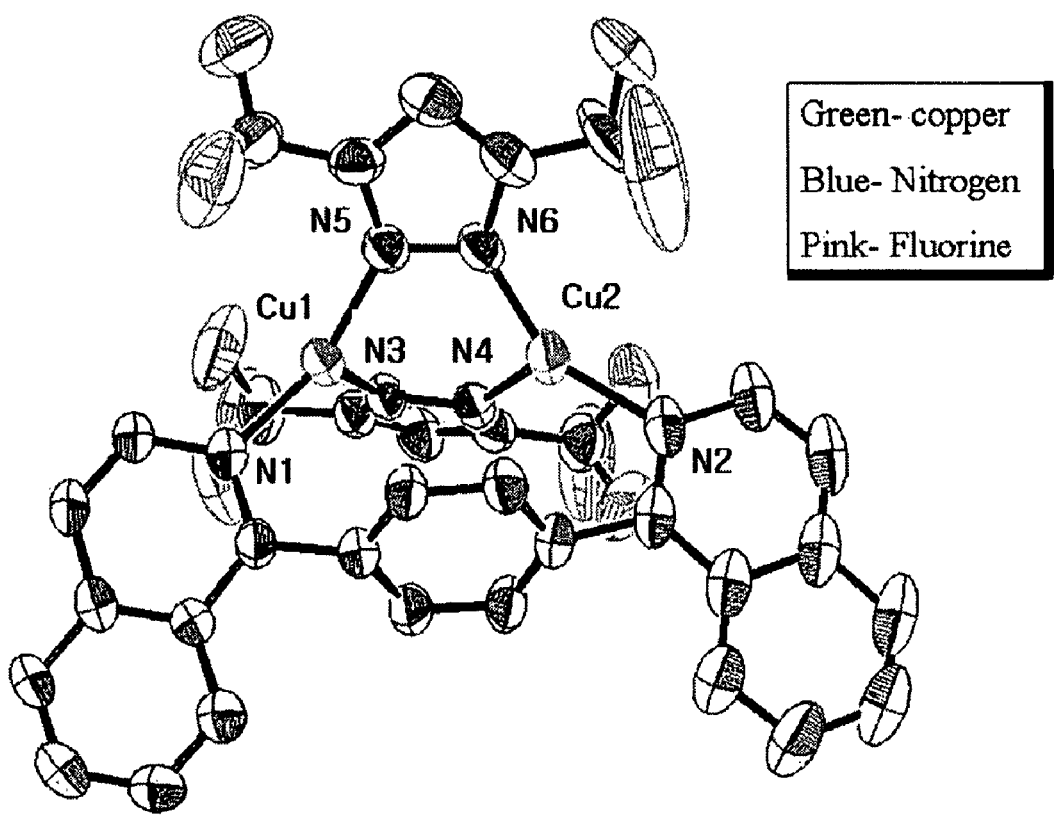
FIG. 12 is a ORTEP diagram of the phosphorescent multinuclear copper complex obtained in Example 3.

The NMR data shows the possibility of the formation of the above two structures. But the crystal structure of the compound obtained from the single crystals made by the slow evaporation from its solution in benzene at low pressure shows the formation of the second structure. The ORTEP diagram of the molecular structure is shown in FIG. 12.

Example 4

Synthesis of Compound $\{[3,5\text{-}(CF_3)_2Pz]Cu\}_{2}[1,4\text{-bis}(2\text{-quinolyl})benzene]$ of Formula 20 and 24

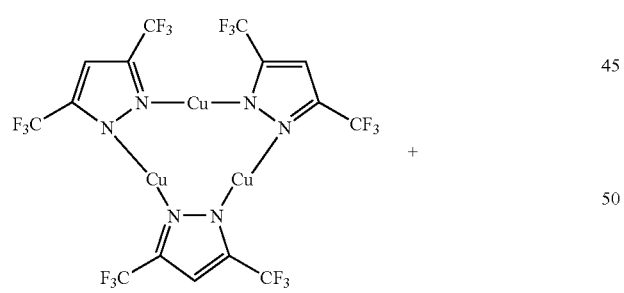

2

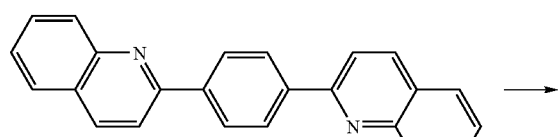

3

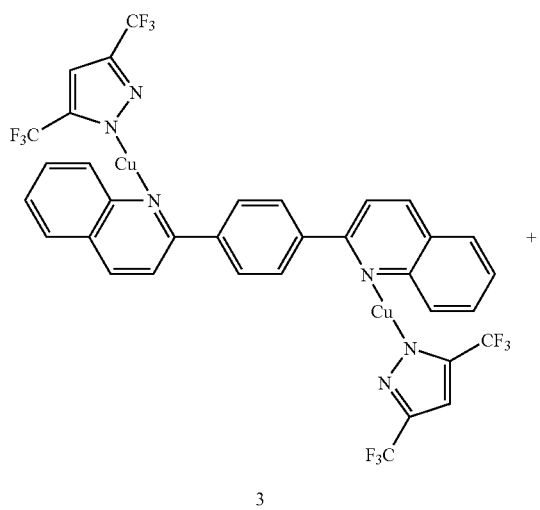

3

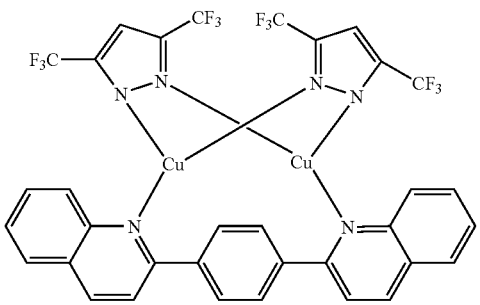

0.160 g (0.2 mmol) of $\{3,5\text{-}(CF_3)_2Pz\text{-}Cu_3\}$ synthesized in Reference Example 1 was reacted with 0.1 g (0.3 mmol) of phenyldiquinoline in 30 mL of benzene for 48 hours. After the reaction terminated, the reaction solution was filtered using Celite and precipitated in hexane to obtain a yellow solid compound of Formula 20 and 24. The yellow solid powder was washed with hexane several times and reprecipitated using a solution of benzene and hexane. The structure of the final product was analyzed and identified through $^1$H NMR spectroscopy.

Example 5

Synthesis of Compound {[3,5-(CF$_3$)$_2$Pz]Cu[4-(2-iosquinolyl)biphenylditoluylamine] of Formula 15

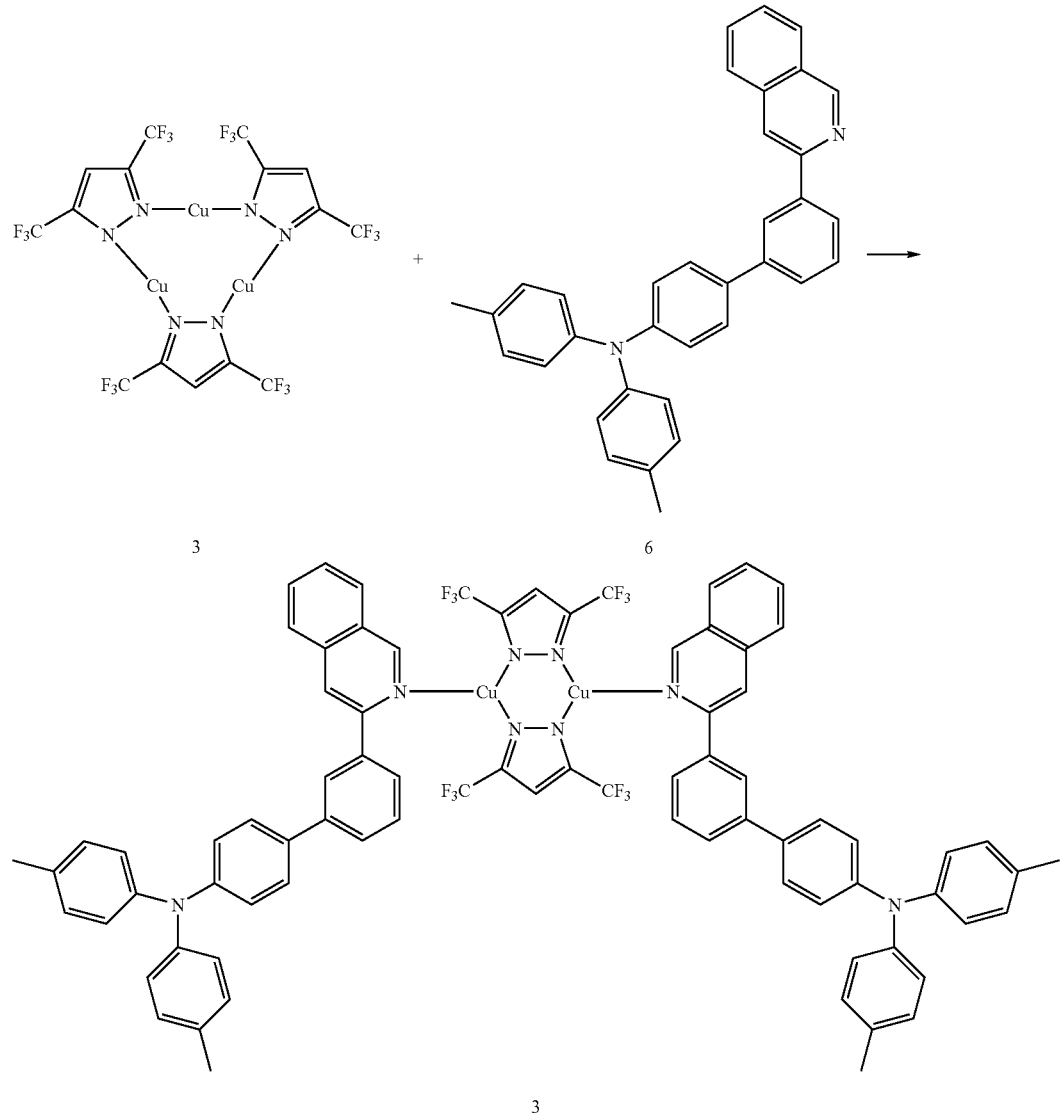

0.160 g (0.2 mmol) of {3,5-(CF$_3$)$_2$Pz}-Cu$_3$} synthesized in Reference Example 1 was reacted with 0.222 g (0.6 mmol) of isoquinolylbiphenyditoluylamine in 30 mL of benzene for 48 hours. After the reaction terminated, the reaction solution was filtered using Celite and precipitated in hexane to obtain a greenish yellow solid compound of Formula 15. The greenish yellow solid powder was washed with hexane several times and reprecipitated using a solution of benzene and hexane. The structure of the final product was analyzed and identified through $^1$H NMR spectroscopy.

$^1$H NMR CDCl$_3$: ppm 8.27 (s, 1H), 8.26 (d, 1H), 8.18 (d, 1H), 8.08 (d, 1H), 7.94 (d, 1H), 7.82 (d, 1H), 7.75 (t, 1H), 7.61 (d, 1H), 7.47 (dd, 4H), 7.0-6.89 (m, 10H), 6.79 (s, 1H)

$^{19}$F NMR CDCl$_3$: ppm −61.15

The photoluminescence of each of the compounds obtained in Examples 1 through 4 was measured using a 10$^{-4}$ M solution of each of the compounds dissolved in methylene chloride. In addition, the compounds were respectively spin-coated on neat films to measure the photoluminescence of each of the compounds in film form.

Figure 5:
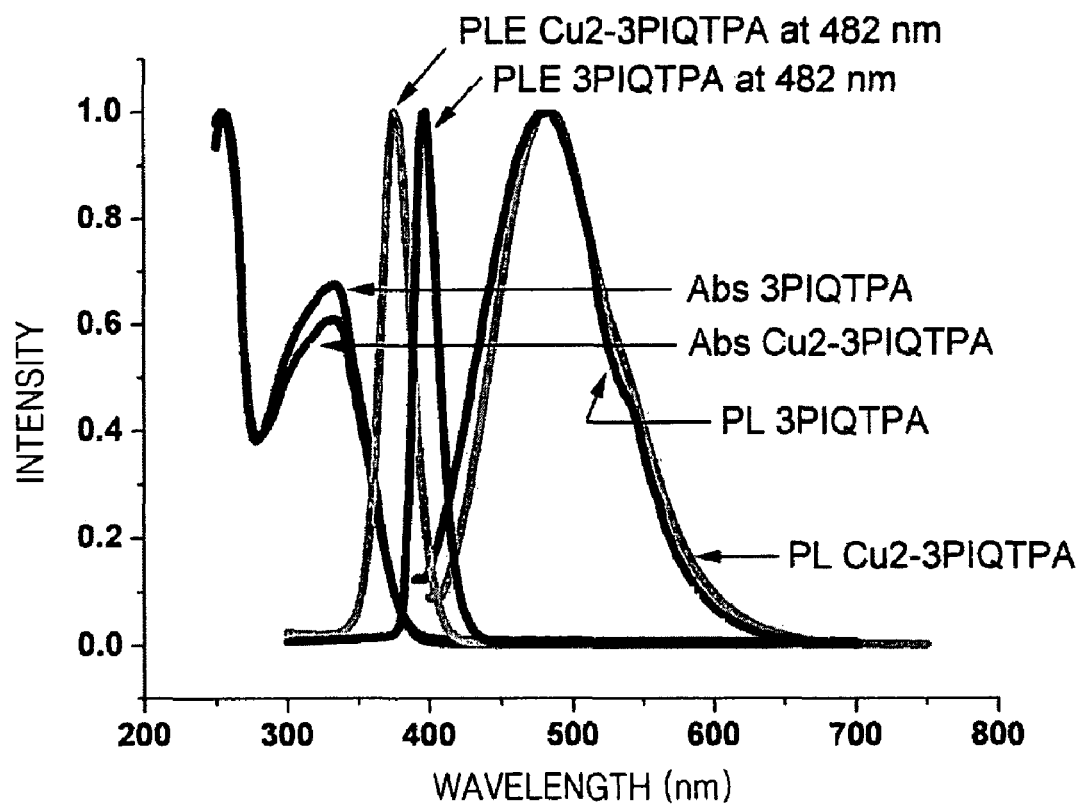
FIG. 5 is an absorption spectrum, a photoluminescence (PL) spectrum, and a PL excitation (PLE) spectrum of the phosphorescent multinuclear copper complex obtained in Example 1.
Figure 8:
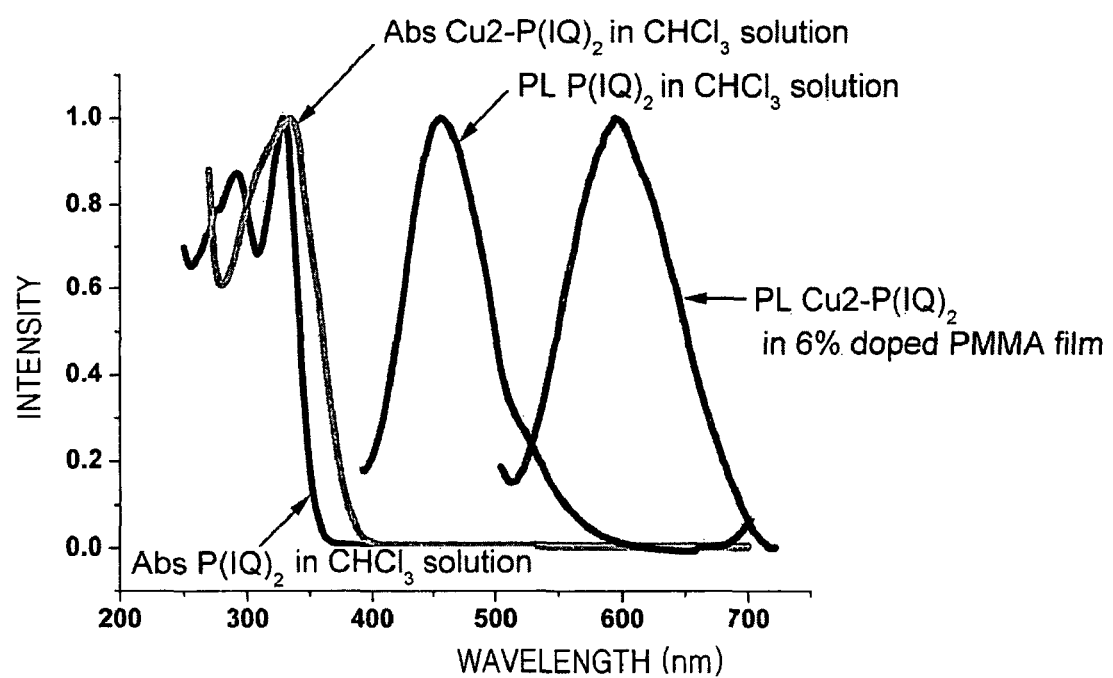
FIG. 8 is an absorption spectrum and a PL spectrum of the phosphorescent multinuclear copper complex obtained in Example 3.

The photoluminescence (PL) and color coordinates (CIE) of the compounds obtained in Examples 1 through 4 are summarized in Table 1. The PLs of the compounds obtained in Examples 1 and 3 are also illustrated in FIGS. 5 and 8.

TABLE 1
| Example | PL λ$_{max}$(nm) | | CIE (x, y) | |
|---|---|---|---|---|
| | Solution | Film | Solution | Film |
| Example 1: | 485 | 560 | (0.18, 0.30) | (0.42, 0.53) |
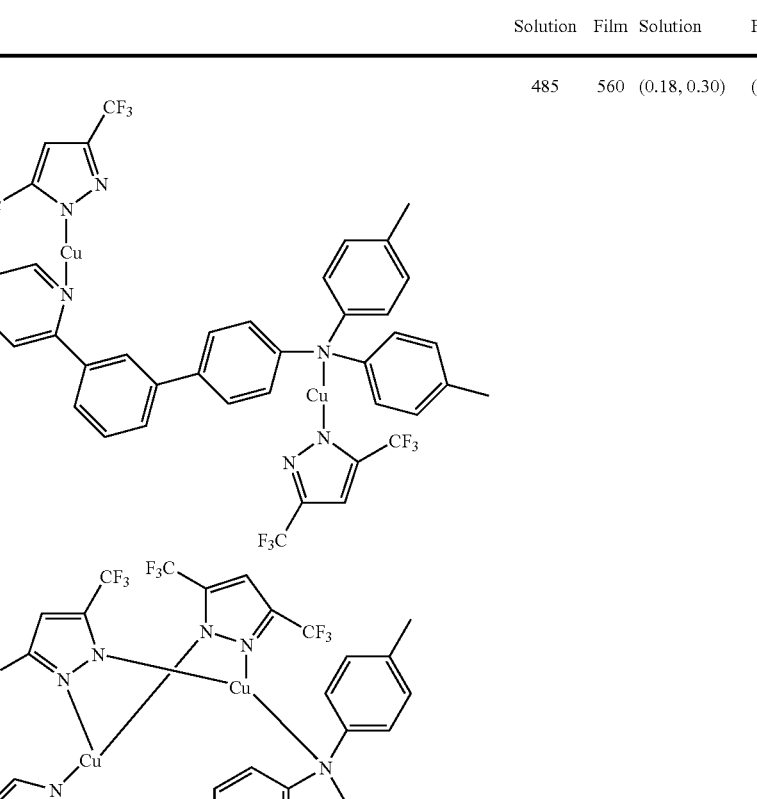
| | | | | |
|---|---|---|---|---|
| Example 2: | 595 | 595 | (0.50, 0.47) | (0.50, 0.46) |
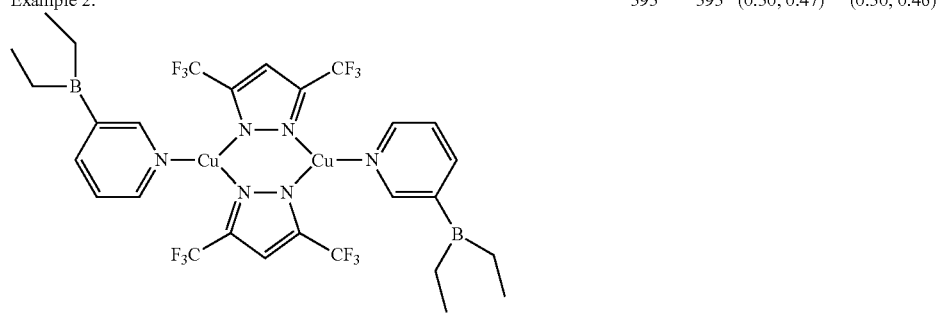

TABLE 1-continued
| Example | PL λ_{max}(nm) Solution | Film | CIE (x, y) Solution | Film |
|---|---|---|---|---|
| Example 3 | 600 | 600 | (0.52, 0.45) | (0.53, 0.46) |
| Example 4 | 585 | 585 | (0.48, 0.42) | (0.47, 0.44) |
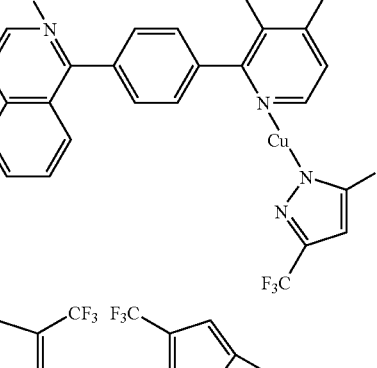
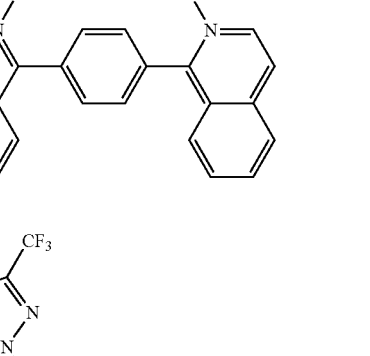

As is apparent from Table 1, the multinuclear copper complexes according to the embodiments of the present invention can produce dopants having excellent photoluminescent characteristics, and are suitable as photoluminescent materials emitting light in the yellow to red wavelength region (560 nm to 630 nm).

Figure 4:
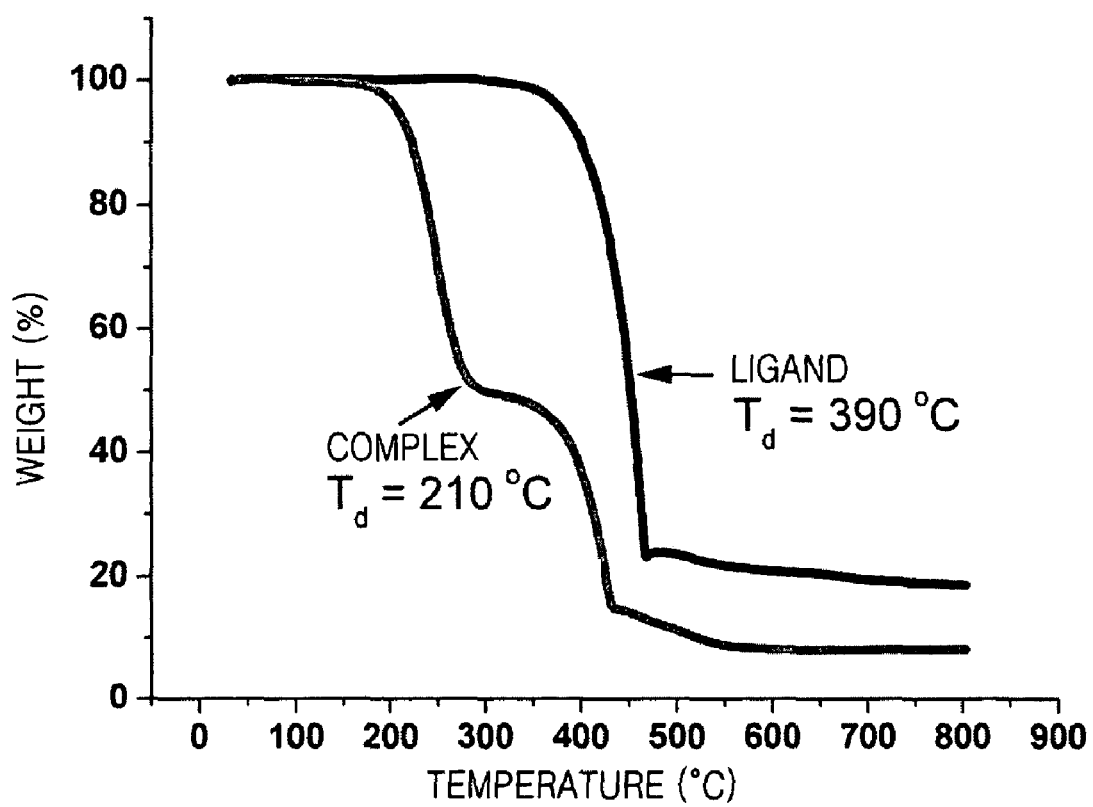
FIG. 4 is a graph of the result of a thermal gravity analysis on the phosphorescent multinuclear copper complex obtained in Example 1.
Figure 7:
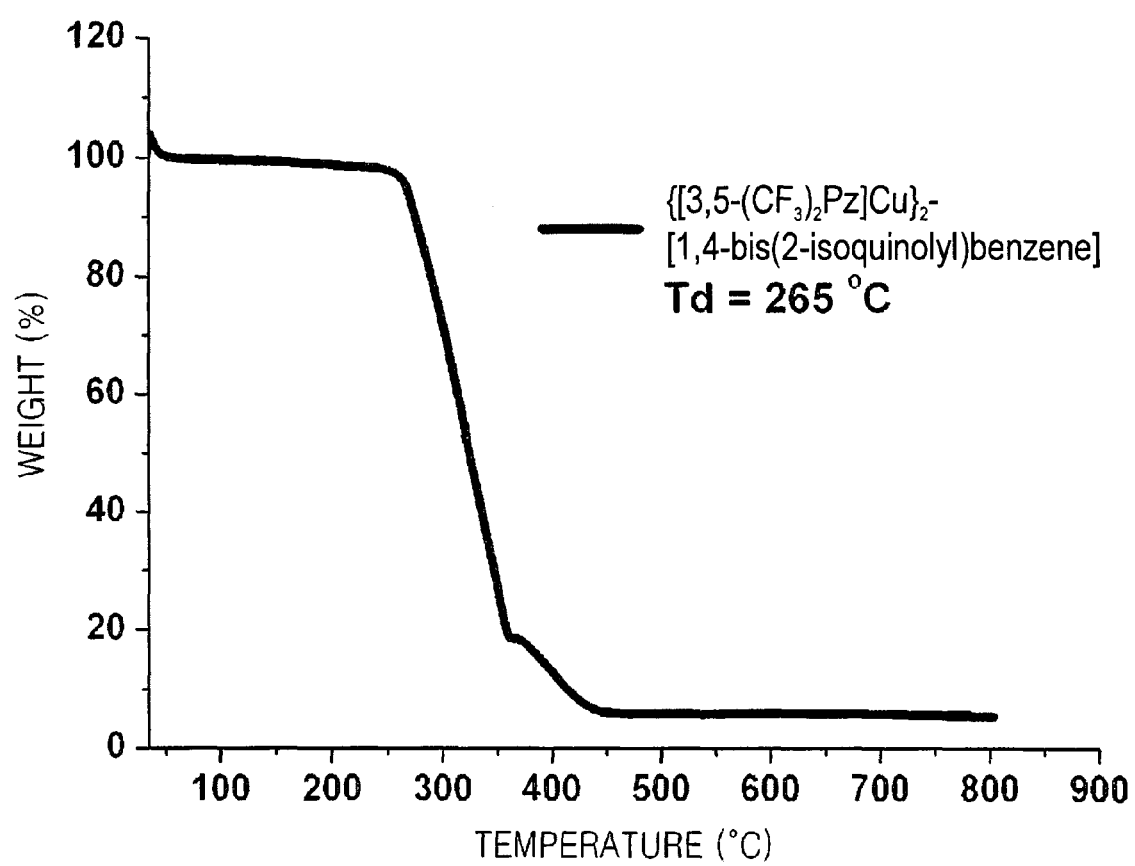
FIG. 7 is a graph of the result of a thermal gravity analysis on a phosphorescent multinuclear copper complex obtained in Example 3.

A thermal gravity analysis was performed on the multinuclear copper complexes obtained in Examples 1 and 3. The results are shown in FIGS. 4 and 7. The multinuclear copper complexes obtained in Examples 1 and 3 had excellent thermal stabilities with a decomposition temperature of 210° C. and 265° C., respectively.

Manufacture of Organic EL Device

Example 6

An indium-tin oxide (ITO)-coated transparent electrode substrate was washed, and an ITO electrode pattern was formed by patterning the ITO layer using a photoresist resin and an etchant and washed. PEDOT{poly(3,4-ethylenedioxythiophene)}[CH 8000] was coated on the washed structure to a thickness of about 50 nm and baked at 120° C. for about 5 minutes to form a hole injecting layer.

A solution of 8% dopant (Example 1) and hosts (mHost5:PBD:TPD=12:8:3) dissolved in chloroform was spin-coated on the hole injecting layer and baked at 100° C. for 1 hour. The solvent was completely removed from the coated layer in a vacuum oven to form an emitting layer having a thickness of 50 nm.

Next, TPBI was vacuum-deposited on the emitting layer using a vacuum deposition apparatus under a pressure of $4\times10^{-6}$ torr or less to form an electron transporting layer having a thickness of 45 nm. Next, LiF was vacuum-deposited on the electron transporting layer at a rate of 0.1 Å/sec to form an electron injecting layer having a thickness of 0.8 nm.

Subsequently, Al was deposited at a rate of 10 Å/sec to form an anode having a thickness of 150 nm. Finally, the resulting structure was encapsulated, thereby resulting in an organic EL device. Here, the encapsulating process was performed by putting BaO powder into a metal can, forming a sealant on the edge of the substrate, and sealing the metal can using a UV hardener in a glove box under a dry nitrogen gas atmosphere to encapsulate the structure.

Figure 2:
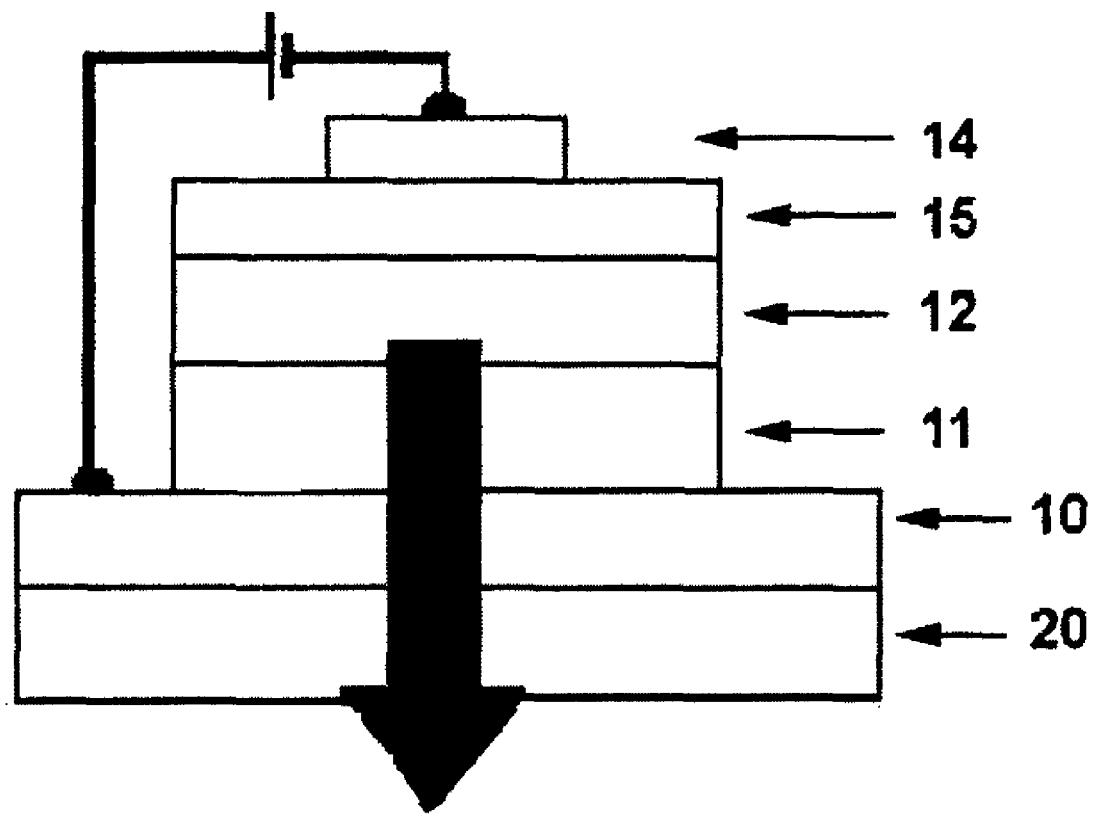
FIG. 2 is a diagram illustrating an organic EL device according to an embodiment of the present invention.

The organic EL device had a multi-layered structure as illustrated in FIG. 2, and a light emission area of 6 mm².

Example 7

An organic EL device was manufactured in the same manner as in Example 6, except that the compound of Formula 3 instead of the compound of Formula 1 was used.

The electroluminescence characteristics, color coordinate (CIE), luminance efficiency, turn-on voltage, and brightness of the organic EL devices manufactured in Examples 5 and 6 are shown in Table 2.

TABLE 2

|  | EL $\lambda_{max}$ (nm) | CIE (x, y) | Luminance efficiency (Cd/A) | Turn-on voltage (V) |
|---|---|---|---|---|
| Example 6 | 600 | (0.53, 0.43) | 0.7 at 11.0 V | 9 |
| Example 7 | 600 | (0.52, 0.45) | 2.8 at 5.0 V | 4.6 |

As is apparent from Table 2, the organic EL devices of Examples 6 and 7 respectively containing the compound of Example 1 and the compound of Example 3 have a high brightness in the yellow to red wavelength region of 560 nm to 630 nm, can operate at a low voltage, and have a high luminance efficiency at a high voltage.

Figure 6:
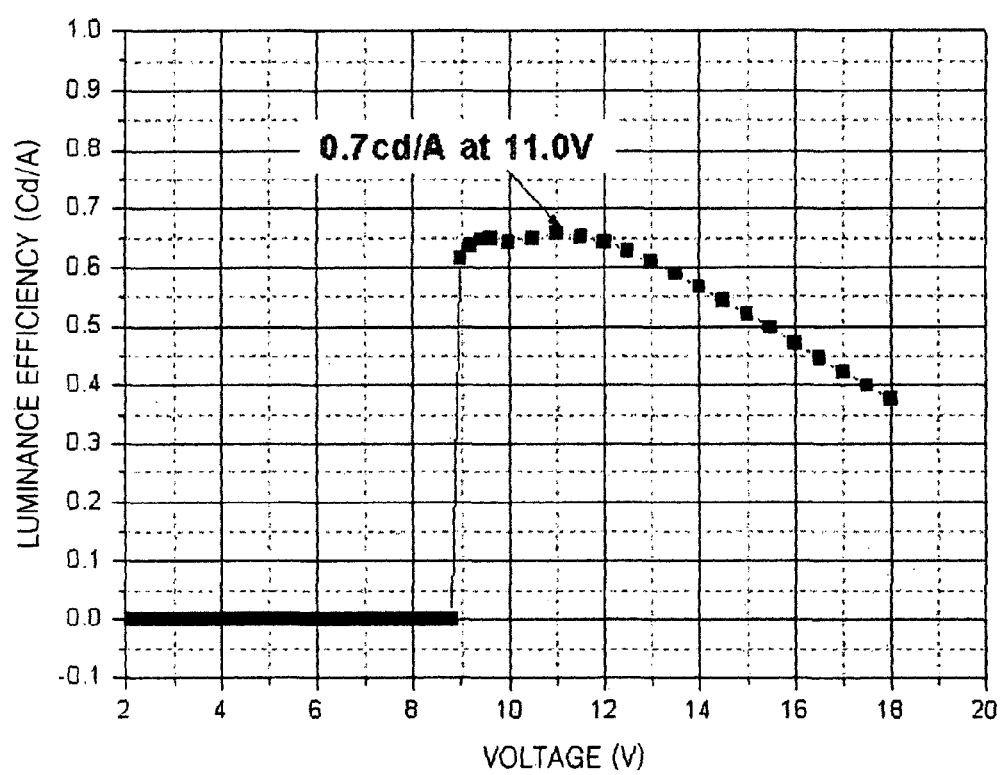
FIG. 6 is a graph of electroluminescence of an organic EL device using the phosphorescent multinuclear copper complex obtained in Example 1.
Figure 11:
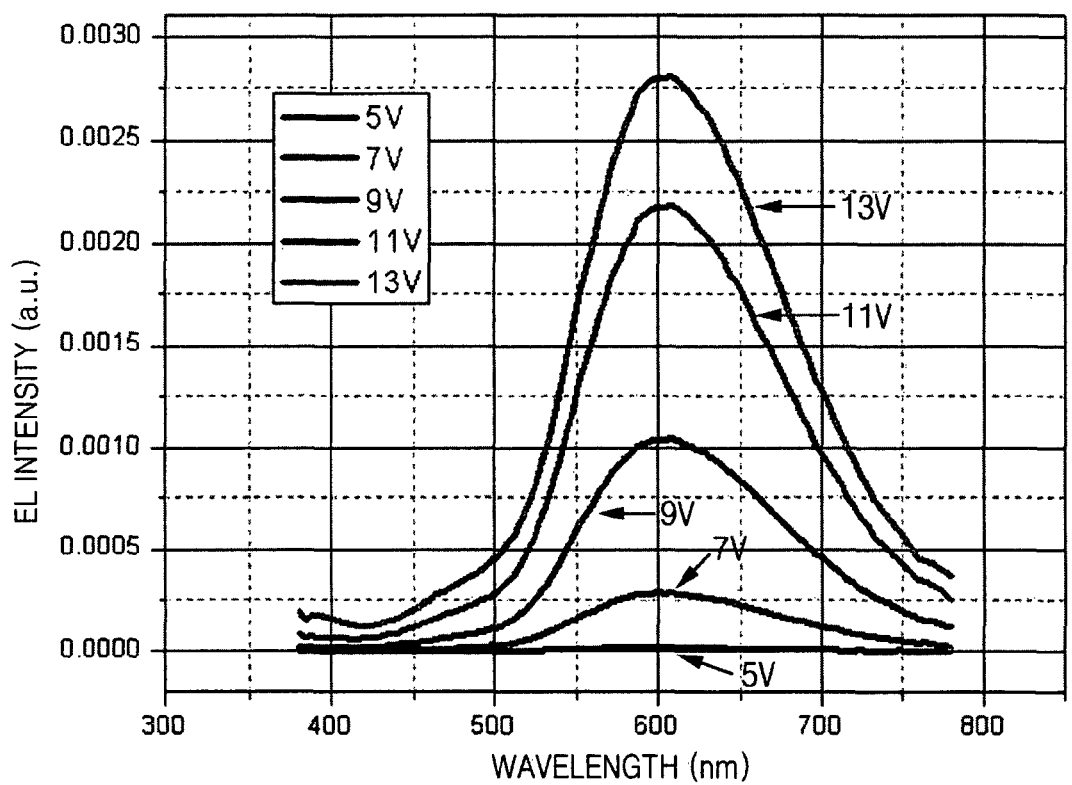
FIG. 11 is a graph of electroluminescence of an organic EL device using the phosphorescent multinuclear copper complex obtained in Example 3.

A change in electroluminescence intensity of the organic EL devices manufactured in Examples 5 and 6 with respect to wavelength, and a change in luminance efficiency of the organic EL devices manufactured in Examples 6 and 7 with respect to voltage are illustrated in FIGS. 6 and 11, respectively. When the multinuclear copper complexes according to the present invention are used as dopants, there are improvements in all the characteristics described above.

As described above, a multinuclear copper complex according to the present invention can efficiently emit light in the yellow to red wavelength region of 560 nm to 630 nm. The multinuclear copper complex can be used to form an organic layer of an organic EL device and can emit light in the yellow to red wavelength region of 560 nm to 630 nm as a high-efficient phosphorescent material. The multinuclear copper complex can emit white light when used together with a green luminescent material or a blue luminescent material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A multinuclear copper complex represented by one of Formulae 1 through 2:

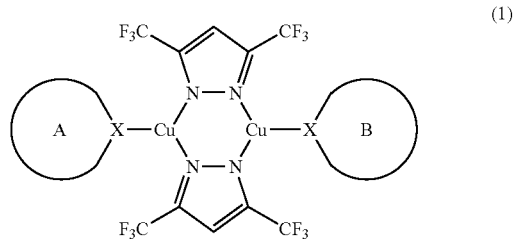

(1)

where A and B of Formula 1 are each independently a $C_2$-$C_6$ heteroaromatic ring containing a hetero atom X and having at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety; and X of A and X of B in Formula 1 are independently N, P, S, or O;

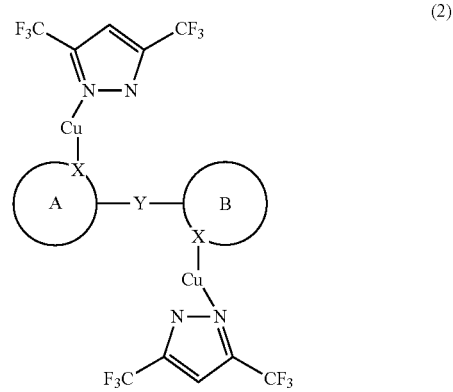

(2)

where A and B of Formula 2 are the same or different and are each a substituted or unsubstituted heteroaromatic ring containing a hetero atom X or a substituted or unsubstituted aliphatic or aromatic group bonded to X, and A and B of Formula 2 optionally have at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety;

X of A and X of B in Formula 2 are independently N, P, S, or O; and

Y is a bond or a group selected from the group consisting of a substituted or unsubstituted $C_1$-$C_{20}$ alkylene group, a substituted or unsubstituted $C_6$-$C_{20}$ arylene group, a substituted or unsubstituted $C_5$-$C_{20}$ cycloalkylene group, a substituted or unsubstituted $C_1$-$C_{20}$ heteroarylene group, a silyl group, and a boryl group.

2. An organic electroluminescent device comprising an organic layer between a pair of electrodes, the organic layer containing the multinuclear copper complex of claim 1.

3. The organic electroluminescent device of claim 2, wherein the organic layer is an emitting layer.

4. The organic electroluminescent device of claim 3, wherein the amount of the multinuclear copper complex is in a range of 1 to 30 parts by weight based on 100 parts by weight of the emitting layer forming material.

5. The organic electroluminescent device of claim 2, wherein the organic layer further comprises at least one host selected from the group consisting of a polymer host, a mixed host of a polymer and a low-molecular weight material, a low-molecular weight host, and a non-emitting polymer matrix.

6. The organic electroluminescent device of claim 2, wherein the organic layer further comprises one of a green luminescent material and a blue luminescent material.

7. A multinuclear copper complex represented by Formula 1:

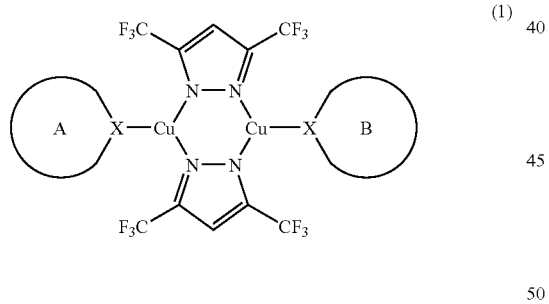

(1)

where A and B are each independently a $C_2$-$C_6$ heteroaromatic ring containing a hetero atom X and having at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety; and X of A and X of B are independently N, P, S, or O.

8. The multinuclear copper complex of claim 7, wherein each of

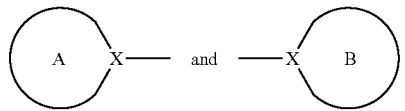

in Formula 1 is independently represented by one of the Formulae 4 through 14:

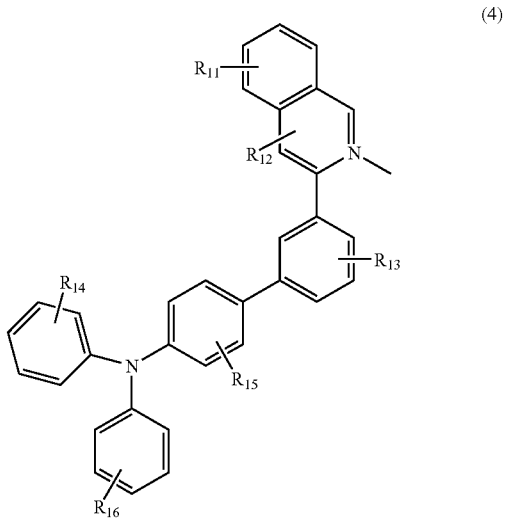

(4)

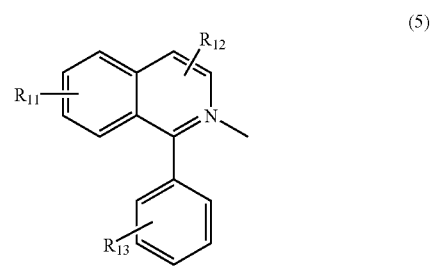

(5)

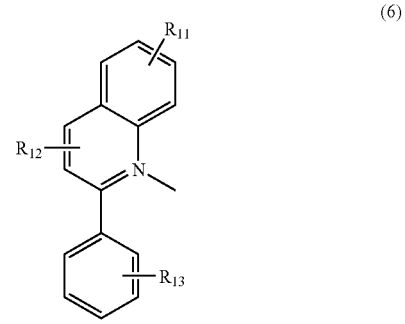

(6)

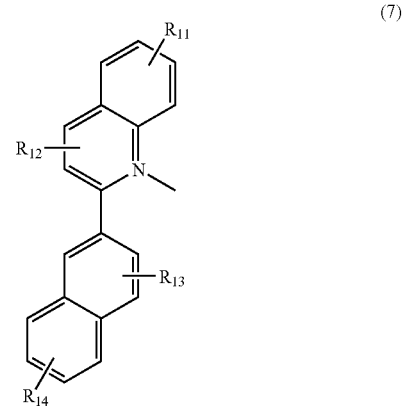

(7)

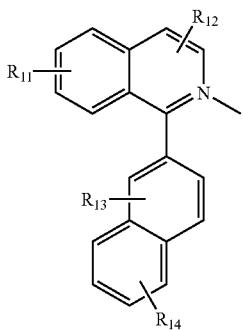 (8)

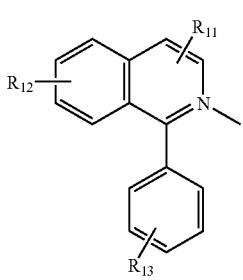 (9)

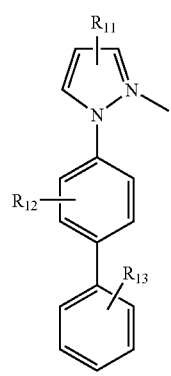 (10)

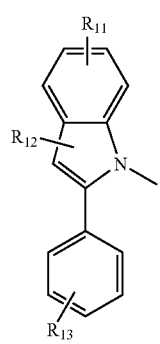 (11)

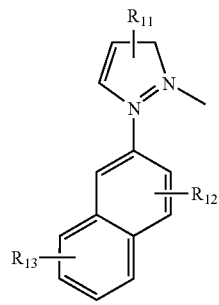 (12)

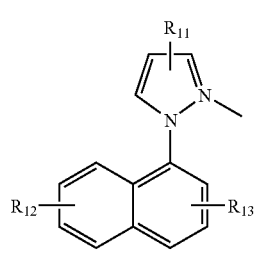 (13)

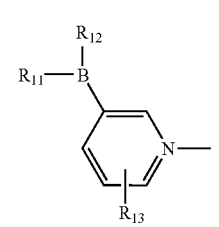 (14)

where $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

9. The multinuclear copper complex of claim 7, being one of compounds represented by Formulae 15 and 16:

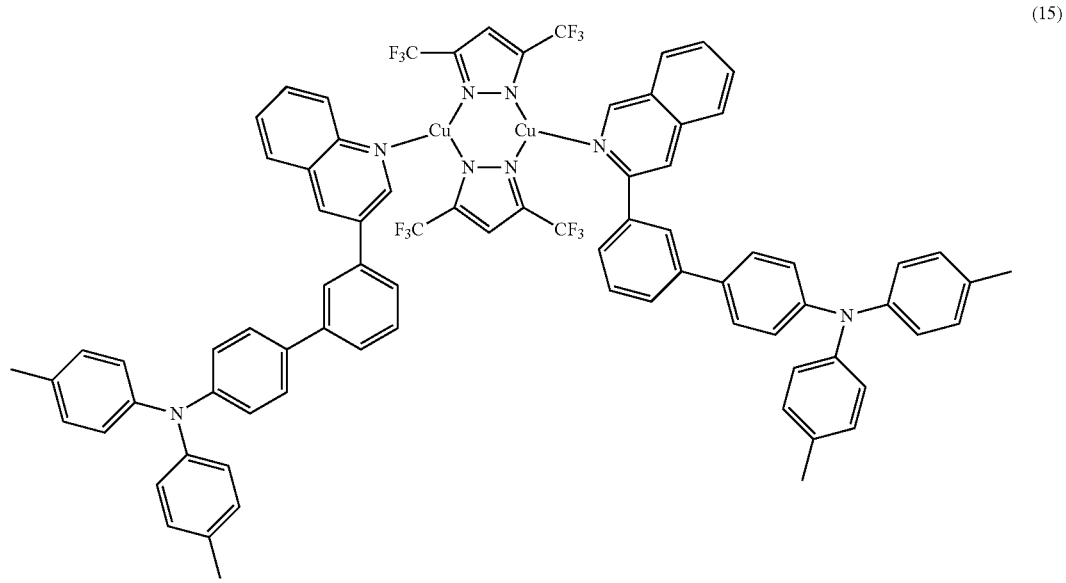

(15)

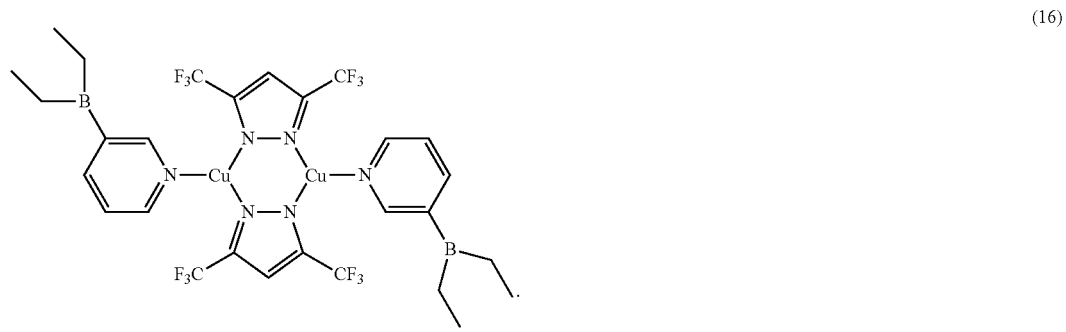

(16)

10. The multinuclear copper complex of claim 7, wherein said at least one substituent is selected from the group consisting of cyclohexyl, cyclopentyl, cyclooctyl, phenyl, 1,3-benzodioxole, biphenyl, naphthalene, anthracene, azulene, thiophene, furan2(5H)-furanone, pyridine, coumarin, imidazole, 2-phenylpyridine, 2-benzothiazole, 2-benzoxazole, 1-phenylpyrazole, 1-naphthylpyrazole, 5-(4-methoxyphenyl)pyrazole, 2,5-bisphenyl-1,3,4-oxadiazole, 2,3-benzofuran and 2-(4-biphenyl)-6-phenyl benzoxazole.

11. The multinuclear copper complex of claim 7, wherein the silyl group is triarylsilyl or trialkylsilyl;
   the boryl group is dialkylboryl, diarylboryl, difluoroboryl, or difluoroheteroarylboryl; and
   the hole transporting moiety is selected from the group consisting of quinolyl, substituted quinolyl, imidazolyl, substituted imidazolyl, benzimidazolyl, triazolyl, substituted triazolyl, oxazolyl, substituted oxazolyl, 1,10-phenanthrolyl, substituted 1,10-phenanthrolyl, quinoxalinyl, or substituted quinoxalinyl.

12. A multinuclear copper complex represented by Formula 2 or 3:

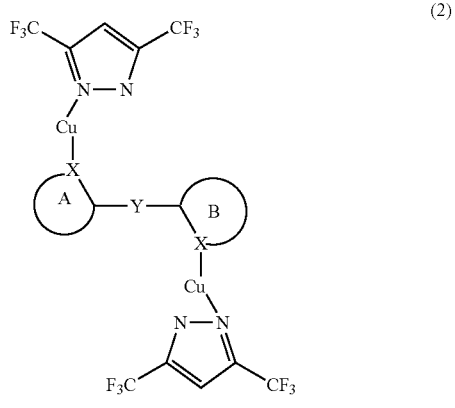

(2)

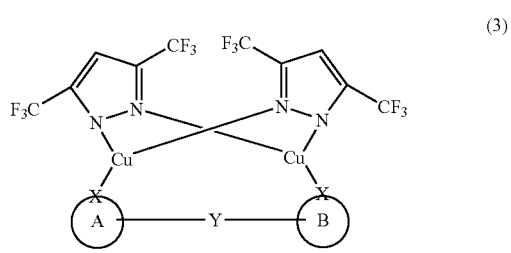

(3)

where A and B are the same or different and are each a substituted or unsubstituted heteroaromatic ring containing a hetero atom X or a substituted or unsubstituted aliphatic or aromatic group bonded to X, and A and B optionally have at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety;

X of A and X of B are independently N, P, S, or O; and

Y is a bond or a group selected from the group consisting of a substituted or unsubstituted $C_1$-$C_{20}$ alkylene group, a substituted or unsubstituted $C_6$-$C_{20}$ arylene group, a substituted or unsubstituted $C_5$-$C_{20}$ cycloalkylene group, a substituted or unsubstituted $C_1$-$C_{20}$ heteroarylene group, a silyl group, and a boryl group.

13. The multinuclear copper complex of claim 12, wherein

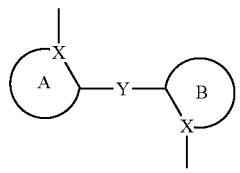

in Formula 2 or 3 is one of the groups represented by Formulae 17 through 19:

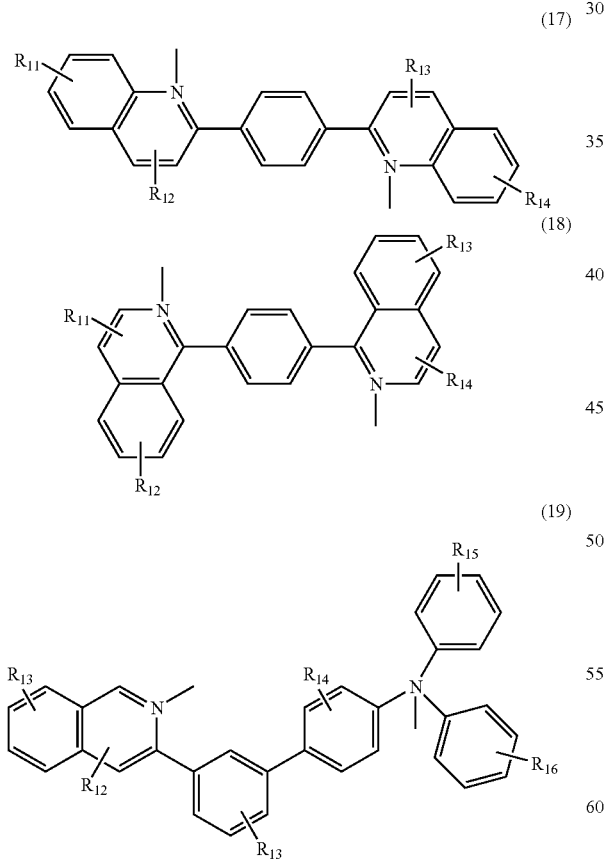

where $R_{11}$, $R_{12}$, $R_{13}$, $R_{14}$, $R_{15}$, and $R_{16}$ are each independently selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group; and R is selected from the group consisting of hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

14. The multinuclear copper complex of claim 12, wherein the silyl group is triarylsilyl or trialkylsilyl;

the boryl group is dialkylboryl, diarylboryl, difluoroboryl, or difluoroheteroarylboryl; and the hole transporting moiety is selected from the group consisting of quinolyl, substituted quinolyl, imidazolyl, substituted imidazolyl, benzimidazolyl, triazolyl, substituted triazolyl, oxazolyl, substituted oxazolyl, 1,10-phenanthrolyl, substituted 1,10-phenanthrolyl, quinoxalinyl, or substituted quinoxalinyl.

15. The multinuclear copper complex of claim 12, being one of compounds represented by Formulae 20 through 25:

[Formula 20]

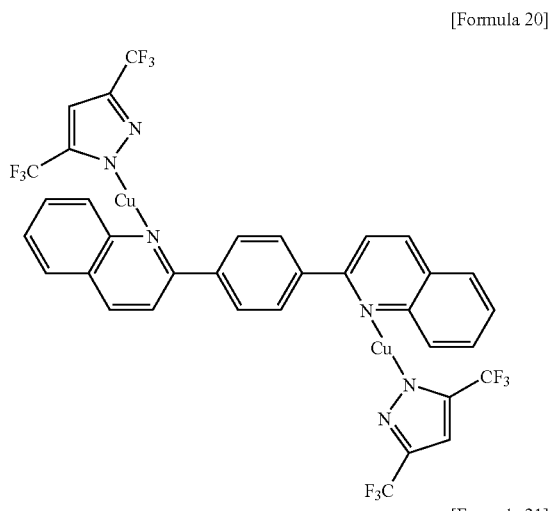

[Formula 21]

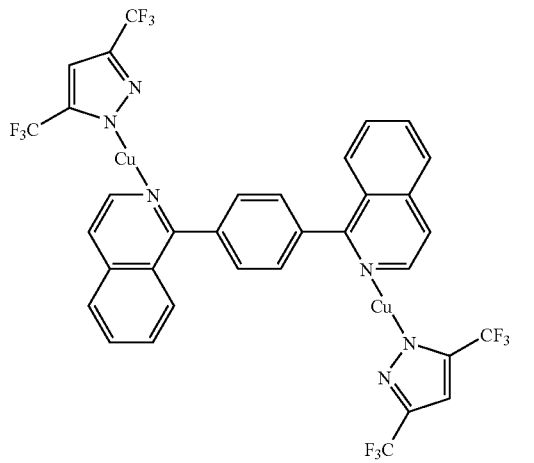

-continued

[Formula 22]
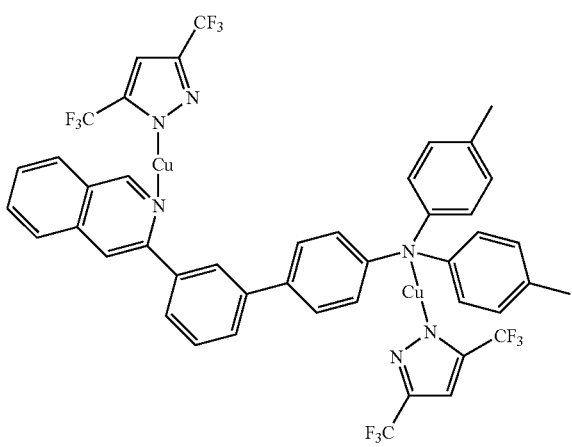

[Formula 23]
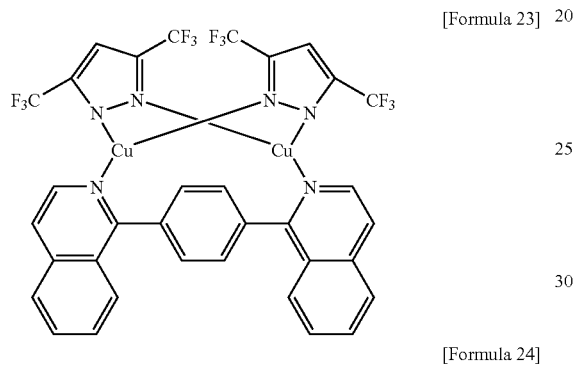

[Formula 24]
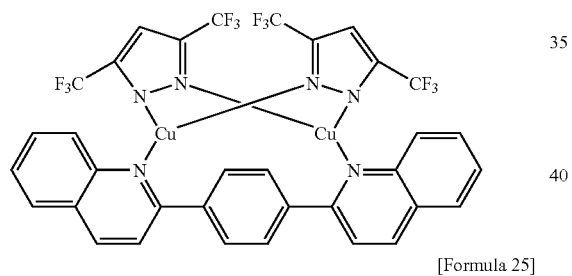

[Formula 25]
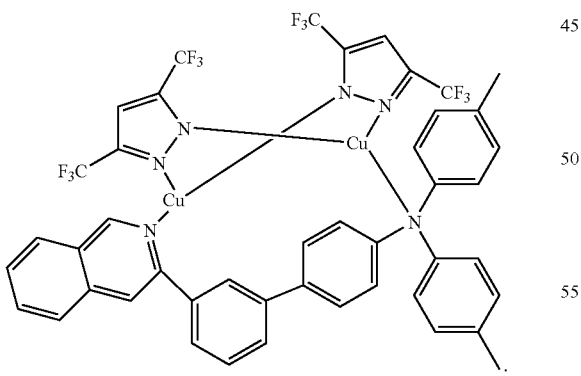

16. The multinuclear copper complex of claim 12, wherein the aliphatic or aromatic group bonded to X for A and B is independently a $C_5$-$C_{20}$ alkyl group, a $C_6$-$C_{20}$ aryl group, a $C_1$-$C_{20}$ heteroaryl group, or a $C_3$-$C_{20}$ cycloalkyl group.

17. A method of synthesizing a multinuclear copper complex represented by one of Formulae 1 through 3, the method comprising:

reacting a compound ($\{[3,5\text{-}CF_3]_2Pz\}\text{-}Cu)_3$) of Formula 26 with heteroaromatic ring compounds represented by Formulae 27 and 28 or a compound of Formula 29:

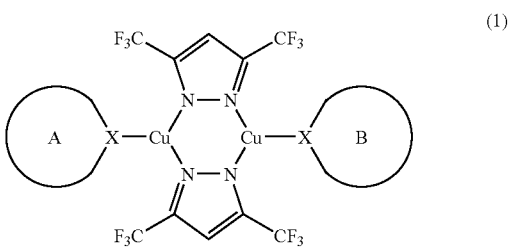
(1)

where A and B of Formula 1 are each independently a $C_2$-$C_6$ heteroaromatic ring containing a hetero atom X and having at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety; and
X of A and X of B in Formula 1 are independently N, P, S, or O;

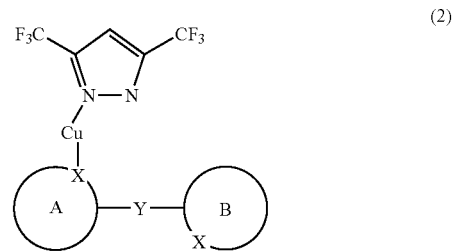
(2)

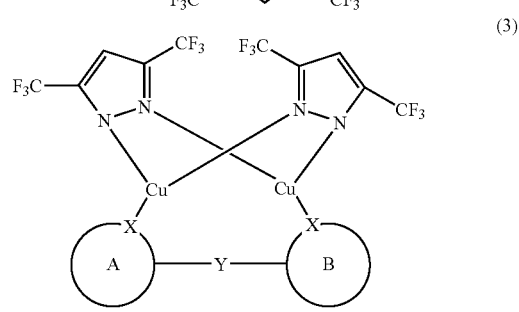
(3)

where A and B of Formulae 2 and 3 are the same or different and are each a substituted or unsubstituted heteroaromatic ring containing a hetero atom X or a substituted or unsubstituted aliphatic or aromatic group bonded to X, and A and B of Formulae 2 and 3 optionally have at least one substituent selected from the group consisting of a $C_5$-$C_{20}$ cycloalkyl group, a $C_6$-$C_{20}$ aryl group, a $C_1$-$C_{20}$ heteroaryl group, a silyl group, a boryl group, and a hole transporting moiety;
X of A and X of B in Formulae 2 and 3 are independently N, P, S, or O; and
Y is a bond or a group selected from the group consisting of a substituted or unsubstituted $C_1$-$C_{20}$ alkylene group, a substituted or unsubstituted $C_6$-$C_{20}$ arylene group, a substituted or unsubstituted $C_5$-$C_{20}$ cycloalkylene group, a substituted or unsubstituted $C_1$-$C_{20}$ heteroarylene group, a silyl group, and a boryl group;

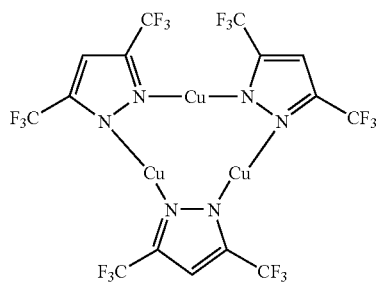 (26)

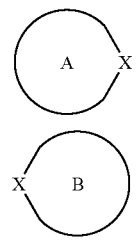 (27)

(28)

where A, B, and X in Formulae 27 and 28 are the same as defined in connection with Formula 1;

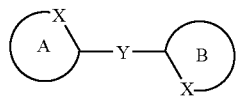 (29)

where A, B, X and Y in Formula 29 are the same as defined in connection with Formula 2 or 3.

18. A multinuclear copper complex represented by one of Formulae 1 and 2 synthesized by the method of claim 17.

19. A multinuclear copper complex represented by Formula 3 synthesized by the method of claim 17.

* * * * *